United States Patent

Hayashibe et al.

(10) Patent No.: US 6,642,264 B1
(45) Date of Patent: Nov. 4, 2003

(54) THIAZOLOBENZOIMIDAZOLE DERIVATIVES

(75) Inventors: Satoshi Hayashibe, Ibaraki (JP); Hirotsune Itahana, Ibaraki (JP); Masamichi Okada, Ibaraki (JP); Atsuyuki Kohara, Ibaraki (JP); Kyoichi Maeno, Ibaraki (JP); Kiyoshi Yahiro, Ibaraki (JP); Itsuro Shimada, Ibaraki (JP); Kazuhito Tanabe, Ibaraki (JP); Kenji Negoro, Ibaraki (JP); Takashi Kamikubo, Ibaraki (JP); Shuichi Sakamoto, Ibaraki (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/958,174
(22) PCT Filed: Apr. 5, 2000
(86) PCT No.: PCT/JP00/02199
§ 371 (c)(1), (2), (4) Date: Oct. 5, 2001
(87) PCT Pub. No.: WO00/59913
PCT Pub. Date: Oct. 12, 2000

(30) Foreign Application Priority Data

Apr. 6, 1999 (JP) ............................................. 11/099062

(51) Int. Cl.[7] ..................... A61K 31/425; C07D 415/02; A61P 43/00
(52) U.S. Cl. ...................... 514/370; 544/133; 548/151; 548/303
(58) Field of Search ................................. 548/151, 303; 514/370; 544/133

(56) References Cited

U.S. PATENT DOCUMENTS 5,843,988 A  12/1998  Annoura et al. ............ 514/454

FOREIGN PATENT DOCUMENTS

| EP | 0 658 539 | 12/1994 | ......... C07C/229/24 |
|---|---|---|---|
| WO | 95/25110 | 9/1995 | ......... C07D/513/02 |
| WO | 97/05109 | 2/1997 | ......... C07D/209/18 |
| WO | 97/05137 | 2/1997 | ......... C07D/473/04 |
| WO | 98/06724 | 2/1998 | ......... C07D/513/04 |

OTHER PUBLICATIONS

Sarhan AO, El–Sherief HA, Mahmoud AM. A convenient one–pot synthesis of 2–benzimidazolylthioacetophenones and thiazolo[3,2-a]benzimidazoles. Tetrahedron. 1996;52:10485–96.*

* cited by examiner

Primary Examiner—Joseph K. McKane
Assistant Examiner—Andrea D. Small
(74) Attorney, Agent, or Firm—Sughrue Mion, PLLC

(57) ABSTRACT

This invention relates to novel thiazolo[3,2-a] benzoimidazole derivatives represented by the following general formula (I). The compounds provided by the invention act specifically on metabotropic glutamate receptors and are used as medicaments. The invention also provides novel compounds useful as intermediates for the synthesis of the compounds of the invention.

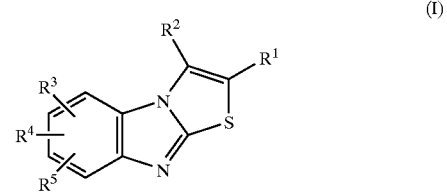

(Symbols in the formula represent the following meanings. $R^1$: carbamoyl, carbonyl, oxy, amino, carbonylamino or the like which may be substituted; $R^2$: hydrogen, lower alkyl or the like; and $R^3$, $R^4$ and $R^5$: hydrogen, lower alkyl and the like which may be the same or different from one another.)

4 Claims, No Drawings

THIAZOLOBENZOIMIDAZOLE DERIVATIVES

This application is a 371 of PCT/JP00/02199 Apr. 5, 2000.

TECHNICAL FIELD

This invention relates to novel thiazolobenzoimidazole derivatives or salts thereof. The compounds of the invention are useful as medicaments, particularly as a metabotropic glutamate receptor ligand.

It further relates to pharmaceutical compositions which comprise the thiazolobenzoimidazole derivatives or salts thereof as an active ingredient and to intermediates for the synthesis of the compounds of the invention.

BACKGROUND ART

Glutamic acid acts as a neurotransmitter in the mammalian central nervous system (Mayer M. L. and Westbrook G. L., Prog. Neurobiol., 28 (1987) 197–276). By the recent studies, importance of glutamic acid in the higher order cranial nerve function has been revealed. Glutamic acid is released from the nerve ending and regulates activity of nerve cells or release of a neurotransmitter, via glutamate receptors which are present in the postsynaptic membrane or nerve ending. Based on various pharmacological and physiological studies, glutamate receptors are currently classified roughly into two categories. One of them is ionotropic receptor and the other is metabotropic receptor (Hollmann M and Heinemann S., Annu. Rev. Neurosci., 17 (1994) 31–108).

Based on the molecular biological studies, it has been reported that the metabotropic glutamate receptor (to be referred to as mGluR hereinafter) exists so far in at least eight different subtypes of from mGluR1 to mGluR8. The mGluR is classified into a group of receptors (mGluR1 and mGluR5) which accelerate production of inositol triphosphate (IP3) and incorporation of calcium ions into cells, by coupling with phospholipase C via G protein, and another group of receptors (mGluR2, mGluR3, mGluR4, mGluR6, mGluR7 and mGluR8) which inhibit production of cAMP by coupling with Gi protein. These receptors show different intracerebral distributions from one another, for example, mGluR6 does not exist in the brain but exists only on the retina, so that it is considered that each receptor is taking each own deferent physiological role. (Nakanishi S., Neuron, 13 (1995) 1031–1037).

Compounds which are selective for the mGluR in comparison with the ionotropic receptor have so far been reported (Hayashi Y. et al., Br. J. Phamacol., 107 (1992) 539–543; Hayashi Y. et al., J. Neurosci., 14 (1995) 3370–3377), and relationships between the mGluR and various morbid states have been reported as the following cases (1) to (4), based on the studies carried out using these compounds.

(1) Epilepsy is induced by the administration of an mGluR agonist (1S,3R)-1-aminocyclopentane-1,3-dicarboxylic acid (to be referred to as (1S,3R)-ACPD hereinafter) (Tizzano J. P. et al., Neurosci. Lett., 162 (1993) 12–16; McDonald J. W. et al., J. Neurosci., 13 (1993) 4445–4455). In addition, the efficacy of (S)-4-carboxy-3-hydroxyphenylglycine (to be referred to as (S)-CHPG hereinafter), which is an antagonist of mGluR1 and also an agonist of mGluR2, in various epilepsy models has been reported (Dalby, N. O. & Thomsen, C. J., J. Pharmacol. Exp. Ther., 276 (1996) 516–522).

(2) Participation of mGluR in the transmission of pain sensation into spinal posterior horn nerve cells has been confirmed by electro-physiological tests (Young, M. R. et al., Neuropharmacology, 33 (1994) 141–144; ibid., 34 (1995) 1033–1041). Also, it has been reported that (S)-CHPG has an action to delay avoiding reaction of thermal and mechanical pain sensation stimulation (Young, M. R. et al., Br. J. Pharmacol., 114 (1995) 316P).

(3) It has been reported that when (1S,3R)-ACPD or (RS)-3,5-dihydroxyphenylglycine (to be referred to as 3,5-DHPG hereinafter) is administered in a trace amount or systemically to the cerebral parenchyma of mouse or rat, it causes nerve cell death accompanied by spasm (Lipartit, M. et al., Life Sci., 52 (1993) PL 85–90; McDonald, J. W. et al., J. Neurosci., 13 (1993) 4445–4455; Tizzano, J. P. et al., Neuropharmacology, 34 (1995) 1063–3067). It is considered that this is a result of the activation of mGluR1 and mGluR5.

(4) It is well known that chronic administration of benzodiazepine forms its dependency. It has been reported that metabolic turnover of inositol-phospholipid increases by (1S,3R)-ACPD via mGluR, on the second day and third day after 7 days of continuous administration of benzodiazepine, and it has been suggested that mGluR is taking a role in the expression of benzodiazepine withdrawal syndrome (Mortensen, M. et al., J. Pharmacol. Exp. Ther., 274 (1995) 155–163).

That is, these reports show that compounds which act upon mGluR1 are useful in epilepsy, pain, nerve cell death inhibition and benzodiazepine withdrawal syndrome.

On the other hand, thiazolobenzoimidazole derivatives have been disclosed in J. Org. Chem., 29 (4) 865–869 (1964); Can. J. Chem., 45 (23) 2903–2912 (1967), Khim. Geterotsikl. Soedin., 7 (3) 393–396 (1971); Indian J. Exp. Biol., 10 (1) 37–40 (1972), Khim. Geterotsikl. Soedin., (6) 778–783 (1974); Synthesis, (3) 189 (1976); Tetrahedron Lett., (3) 275–278 (1977); Bull. Chem. Soc. Jpn., 61 (4) 1339–1344 (1988); J. Prakt. Chem., 330 (3) 338–348 (1988); Bull. Pol. Acad. Sci. chem., 37 (5–6) 185–191 (1989); Chem. Pap., 48 (2) 108–110 (1994), Tetrahedron, 52 (31) 10485–10496 (1996) and the like. However, among these reports, Indian J. Exp. Biol., 10 (1) 37–40 (1972) and Bull. Pol. Acad. Sci. Chem., 37 (5–6) 185–191 (1989) describe that thiazolobenzoimidazole derivatives have antibacterial actions but do not disclose about their use as a medicament, and there is no disclosure or suggestion regarding the action of these thiazolobenzoimidazole derivatives upon metabotropic glutamate receptors.

Regarding compounds having a function as a metabotropic glutamate receptor ligand, on the other hand, a compound having an amino acid or peptide structure (cf. JP-A-7-267908; the term "JP-A" as used herein means an "unexamined published Japanese patent application"), a compound having a thieno[2,3-b]indole structure (cf. WO 95/25110), a cyclopropachromenecarboxylic acid derivative (cf. JP-A-8-169884), a 3-vinylindole derivative (cf. WO 97/05109), a pyridino[2,3-b]indole derivative (cf. WO 97/05137) and an imidazobenzothiazole derivative (cf. WO 98/06724) have so far been reported, but thiazolobenzoimidazole derivatives are not known.

Though these compounds and the like are known as metabotropic glutamate receptor ligand, their actions are still insufficient, so that a compound having more excellent action upon metabotropic glutamate receptors is expected.

The objects of the invention is to provide a thiazolobenzoimidazole derivative which has a novel basal skeleton and shows excellent action upon metabotropic glutamate receptors, and salts thereof, and to further provide a medicament which contains the same.

DISCLOSURE OF THE INVENTION

The present inventors have conducted intensive studies and accomplished the invention by finding that a thiazolobenzoimidazole derivative exerts strong action upon metabotropic glutamate receptors and is useful as a medicament.

Accordingly, the invention relates to a thiazolobenzoimidazole derivative represented by the following general formula (I) or a salt thereof and a pharmaceutical composition which uses the compound as an active ingredient.

A thiazolobenzoimidazole derivative represented by the following general formula (I) or a salt thereof

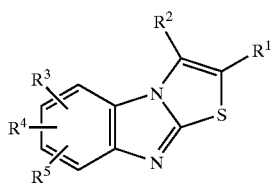

(I)

(wherein each of the symbols means as follows;

$R^1$:
(1) —$A^1$—CO—N($R^6$)—$R^7$,
(2) —$A^1$—CO—$A^2$—$R^8$,
(3) —$A^1$—CO—$A^3$—N($R^6$)—$R^7$,
(4) —$A^1$—O—$A^2$—$R^9$,
(5) —$A^1$—N($R^6$)—$R^7$,
(6) —$A^1$—N($R^6$)—CO—$R^7$, or
(7) —N($R^{10}$)—CO—O—$R^{11}$, $A^1$: the same or different from each other and each represents a bond or a lower alkylene group which may be substituted by hydroxyl group(s), $A^2$: the same or different from each other and each represents a bond, a lower alkylene or lower alkenylene group, $R^6$ and $R^7$: the same or different from each other and each represents hydrogen, —N($R^{15}$)—$R^{16}$, a lower alkyl which may be substituted, a cycloalkyl which may be substituted or a hetero ring which may be substituted and may have bridges(s), with the proviso that $R^6$ and $R^7$, together with the adjacent nitrogen atom, may form a hetero ring which may have a substituent and other hetero atom(s), when $R^1$ is —$A^1$—CO—N($R^6$)—$R^7$, $R^2$ is methyl, $A^1$ is a bond, and one of $R^6$ and $R^7$ is a hydrogen, the other means other than n-propyl substituted by nicotinamide, $R^{15}$ and $R^{16}$: the same or different from each other and each represents hydrogen, —CO-lower alkyl, —CO-halo-lower alkyl or —COOR$^{14}$, $R^8$: a cycloalkyl which may be substituted and may have bridge(s) or a lower alkyl or lower alkenyl substituted by a cycloalkyl which may be substituted and may have 1 or 2 double bonds in the ring, $A^3$: a lower alkylene group which may be substituted by hydroxyl group(s), $R^9$: a lower alkyl which may be substituted, a cycloalkyl or an aryl which may be substituted, $R^{10}$: hydrogen or a lower alkyl group, $R^{11}$: a lower alkyl, or a cycloalkyl which may be substituted, $R^2$: hydrogen, a lower alkyl, a halo-lower alkyl, a hydroxy-lower alkyl, a lower alkyl-O-lower alkyl, an amino-lower alkyl or a (mono- or di-lower alkylamino)-lower alkyl group, $R^3$, $R^4$ and $R^5$: the same or different from one another and each represents hydrogen, a halo, a lower alkyl, a halo-lower alkyl, an $N_3$-lower alkyl, a hydroxy-lower alkyl, hydroxy, a lower alkyl-O—, cyano, —COOR$^{14}$, acyl, a formyl-lower alkyl, an acyl-O—, an acyl-O-lower alkyl, nitro, —$A^4$—N($R^{12}$)—($R^{13}$), —SO$_3$H or —$A^5$—O—$A^4$—N($R^{12}$)—($R^{13}$) group, $R^{12}$ and $R^{13}$: the same or different from each other and each represents hydrogen, a —CO-lower alkyl-N($R^{15}$)—$R^{16}$, a —CO-halo-lower alkyl group, a lower alkyl which may be substituted or a hetero ring group which may be substituted, with the proviso that $R^{12}$ and $R^{13}$, together with the adjacent nitrogen atom, may form a hetero ring which may have a substituent and other hetero atom(s), also, when $R^{12}$ and $R^{13}$ are hydrogen at the same time, $A^4$ represent other than bond, $R^{14}$: hydrogen or a lower alkyl group, $A^4$: a bond or a lower alkylene group which may be substituted by hydroxyl group(s), and $A^5$: a bond or a lower alkylene group).

Preferred is a compound in which $R^1$ in the above general formula (I) is —$A^1$—CO—N($R^6$)—$R^7$ or a salt thereof.

More preferred is a compound, or a salt thereof, selected from 6-{[(2-methoxyethyl)amino]methyl}-N-methyl-N-neopentylthiazolo[3,2-a]benzoimidazole-2-carboxamide, N-cyclohexyl-6-{[(2-methoxyethyl)amino]methyl}-N-methylthiazolo[3,2-a]benzoimidazole-2-carboxamide, 6-{[(3-methoxypropyl)amino]methyl}-N-methyl-N-neopentylthiazolo[3,2-a]benzoimidazole-2-carboxamide, N-cyclohexyl-N-methyl-6-morpholinomethylthiazolo[3,2-a]benzoimidazole-2-carboxamide, methyl N-{[2-[cyclohexyl(methyl)carbamoyl]thiazolo[3,2-a]benzoimidazol-6-yl]methyl}-N-methylglycinate, 6-{[N-(2-methoxyethyl)-N-methylamino]methyl}-N-methyl-N-neopentylthiazolo[3,2-a]benzoimidazole-2-carboxamide, N-cyclohexyl-6-{[N-(2-methoxyethyl)-N-methylamino]methyl}-N-methylthiazolo[3,2-a]benzoimidazole-2-carboxamide and N-({2-[cyclohexyl(methyl)carbamoyl]thiazolo[3,2-a]benzoimidazol-6-yl}methyl)-N-methylglycine.

As another object of the invention, it relates to a pharmaceutical composition which comprises the aforementioned thiazolobenzoimidazole derivative or a pharmaceutically acceptable salt thereof as an active ingredient, preferably a metabotropic glutamate receptor antagonist, more preferably an agent for preventing or treating cerebral infarction, most preferably an agent for treating cerebral infarction acute phase.

As still another object of the invention, it provides the following compounds which are useful as intermediates in synthesizing the aforementioned thiazolobenzoimidazole derivative or a salt thereof.

A compound of the following general formula (Ia) or a salt thereof

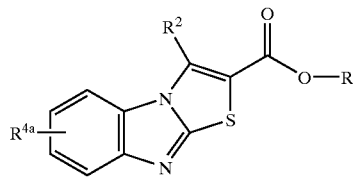

(wherein each of the symbols means as follows;
R: hydrogen or a lower alkyl,
$R^2$: hydrogen or a lower alkyl, and
$R^{4a}$: carboxyl, hydroxymethyl, formyl or substituted silyloxymethyl).

The following further describes the compound represented by the general formula (I). In the definition of general formulae as used herein, unless otherwise noted, the term "lower" means a straight or branched carbon chain having from 1 to 6 carbon atoms.

The "lower alkyl" is a $C_{1-6}$ alkyl, preferably a $C_{1-5}$ alkyl such as methyl, ethyl, propyl, isopropyl, t-butyl or neopentyl, more preferably a $C_{1-3}$ alkyl.

The "lower alkyl" may be substituted, and examples of the substituent include OH, a lower alkyl-O—, amino, a mono- or di-lower alkyl-amino, carboxyl, a lower alkyl-O—C(=O)— and the like.

The "lower alkylene" is a group which further has another bond at an optional position of the above lower alkyl, preferably a $C_{1-3}$ alkylene.

The "lower alkenylene" is a group which has one or more double bonds at optional positions of the above lower alkylene, preferably a $C_{2-4}$ alkenylene.

The "acyl" is formyl or a group represented by lower alkyl-C(=O)—, preferably formyl or a $C_{1-4}$ acyl.

The "halo" means fluorine, chlorine, bromine or iodine atom.

The "aryl" means an aromatic hydrocarbon ring group, preferably a $C_{6-10}$ aryl, more preferably phenyl or naphthyl, most preferably phenyl.

The "cycloalkyl" means a cycloalkyl having from 3 to 8 carbon atoms, and those which have bridge(s) are also included therein. Preferred is a cycloalkyl having 5 or 6 carbon atoms. These cycloalkyl may be substituted with lower alkyl(s).

The "hetero ring together with the adjacent nitrogen atom, which may have other hetero atom(s)" means a saturated hetero ring of five- or six-membered single ring formed by combining $R^6$ with $R^7$, which may have 1 or 2 hetero atoms of oxygen, sulfur and nitrogen atoms, in addition to the nitrogen atom to which $R^6$ and $R^7$ are attached, and also may have 1 or 2 double bonds in the ring, or a condensed saturated hetero ring formed by condensation of these saturated hetero rings with a cycloalkyl, a saturated hetero ring condensed with benzene ring (e.g., tetrahydroquinoline, indoline or the like) or spiro ring.

The "hetero ring" means a saturated hetero ring or a heteroaryl ring.

The "hetero ring which may have bridge(s)" is a hetero ring which has an alkylene or bridge including hetero atom(s), and quinuclidine and the like can be exemplified.

The "saturated hetero ring" means a saturated hetero ring of five- or six-membered single ring having 1 or 2 hetero atoms of oxygen, sulfur and nitrogen atoms as the ring atoms, and its preferred examples include pyrrolidine, piperidine, piperazine, morpholine, thiomorpholine rings or the like.

The "heteroaryl" means a five- or six-membered single ring or condensed ring heteroaryl group having 1 or 2 hetero atoms of oxygen, sulfur and nitrogen atoms, in addition to the nitrogen atom to which $R^5$ and $R^6$ are attached, and its preferred examples include pyrrole, imidazole, pyrazole, isothiazole, isoxazole, pyridine, pyrazine, pyrimidine, pyridazine and the like. More preferred is a heteroaryl of five-membered single ring having one nitrogen atom as the other ring atom.

The "spiro ring" means a spiro ring composed of a hetero ring or a cycloalkyl, preferably a bicyclic Spiro ring composed of a saturated hetero ring and a cycloalkyl.

The substituent of a group which may be substituted or may have a substituent is as follows.

The substituent means a usual substituent of a group to be substituted commonly used in this field, and its examples include a lower alkyl which may be substituted with OH, a halo-lower alkyl, OH, a lower alkyl-O—CO—, a lower alkyl-O—, a —O-lower alkyl-O—, a —O-aralkyl, a lower alkylthio, a —$SO_2$-lower alkyl, a halo, cyano, $NO_2$, $NH_2$, a mono- or di-lower alkyl-amino, a substitutable aralkyl, a substitutable cycloalkyl, a substitutable aryl, an —O-substitutable aryl, an —S-substitutable aryl, an —$SO_2$-substitutable aryl, an —NH—$SO_2$-substitutable aryl, a substitutable hetero ring, an —O-hetero ring, an —S-hetero ring, an —$SO_2$-hetero ring, an —NH—$SO_2$-hetero ring, oxo, acyl, acyl-O—, COOH, a lower alkyl-O-lower alkyl and the like.

Preferably, it is selected from a class consisting of a halo, a lower alkyl, a halo-lower alkyl, hydroxy, a hydroxy-lower alkyl, a lower alkyl-O—, oxo, acyl, acyl-O—, COOH, a lower alkyl-O—CO—, a lower alkyl-O-lower alkyl, $NO_2$, cyano, $NH_2$, a mono- or di-lower alkyl-amino and a substitutable hetero ring. The number of substituents is not particularly limited, when it can be substituted, but is preferably from 1 to 4.

The "mono- or di-lower alkyl-amino" means an amino group substituted with 1 or 2 of the aforementioned lower alkyl.

The "substituted silyloxymethyl" means a silyloxymethyl group substituted with a lower alkyl or an aryl.

Depending on the kind of groups, the compound of the invention exists in optical isomer forms (optically active substances, diastereomers and the like). In addition, a compound having amido bond is included in the compound of the invention, so that tautomers based on the amido bond also exist. These isomers in the isolated or mixed form are included in the invention.

The compound of the invention forms a salt with an acid or a base. Examples of the salt with an acid include acid addition salts with inorganic acids (e.g., hydrochloric acid, hydrobromic acid, hydroiodic acid, sulfuric acid, nitric acid, phosphoric acid and the like) or with organic salts (e.g., formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid and the like).

Examples of the salt with a base include salts with inorganic bases such as sodium, potassium, magnesium, calcium, aluminum and the like, with organic bases such as methylamine, ethylamine, meglumine, ethanolamine and the like, or with basic amino acids such as lysine, arginine, ornithine and the like, as well as an ammonium salt. In addition, the compound of the invention can form hydrates, solvates such as with ethanol and the like and polymorphism.

In addition, a pharmacologically acceptable prodrug is included in the compound of the invention. Examples of the group which forms the pharmacologically acceptable prodrug of the compound of the invention include the groups described in *Prog. Med.,* 5: 2157–2161 (1985) and the groups described in "Development of Drugs" vol. 7, Molecular Designing, pp. 163–198, published in 1990 by Hirokawa Shoten. Illustratively, it is a group which can be converted into the primary amine, secondary amine, OH, COOH or the like of the invention by hydrolysis or solvolysis or under a physiological condition, and its examples in the case of a prodrug of OH group include —OCO-lower alkylene which may be substituted-COOR (R represents H or a lower alkyl, the same shall apply hereinafter), —OCO-lower alkenylene which may be substituted-COOR, —OCO-aryl which may be substituted, —OCO-lower alkylene-O-lower alkylene-COOR, an —OCO—COR, —OCO-lower alkyl which may be substituted, —OSO$_2$-lower alkylene which may be substituted-COOR, —O-phthalidyl, 5-methyl-1,3-dioxolen-2-on-4-yl-methyloxy and the like.

Also, the compound of the invention has properties which are more suitable for its clinical use, and a compound having excellent water-solubility is also included in the compound of the invention.

Production Method

The compound (I) of the invention and synthesis intermediates thereof can be produced by the following production methods.

(In the following description, DMF is abbreviation for dimethylformamide, and DMSO for dimethyl sulfoxide, THF for tetrahydrofuran, TFA for trifluoroacetic acid, DCE for 1,2-dichloroethane, Tol for toluene, EtOAc for ethyl acetate, Py for pyridine and TEA for triethylamine.)

(First Production Method: Production of thiazolo[3,2-a]benzoimidazole Ring)

(Scheme 1)

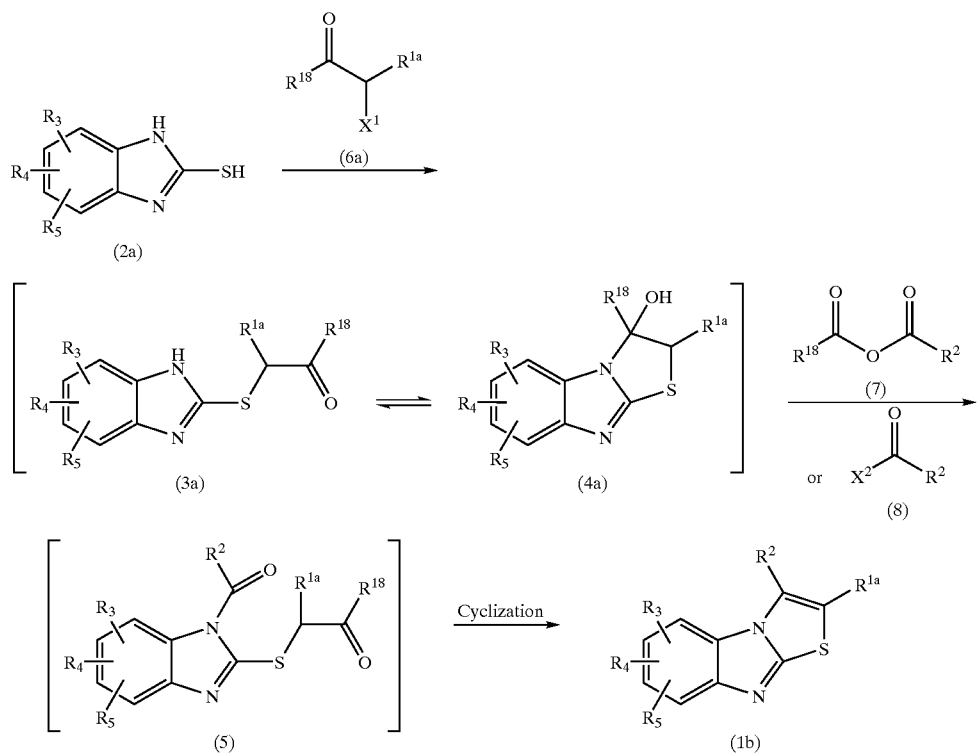

(Scheme 2)

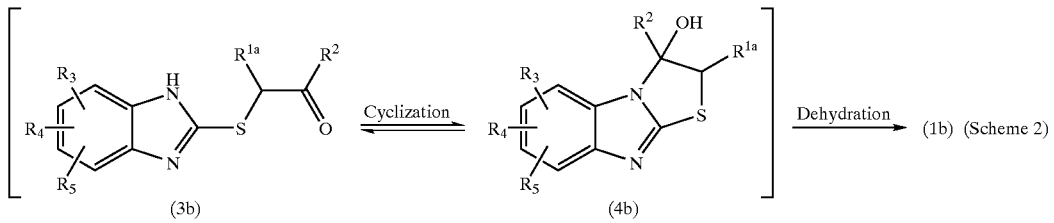

(Scheme 3)

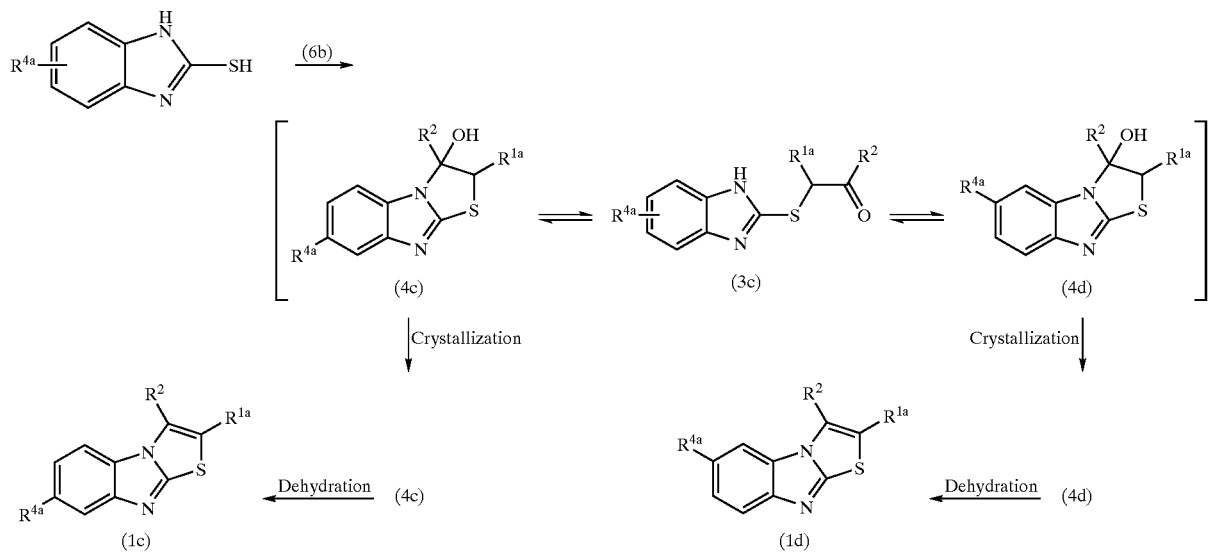

(Scheme 4)

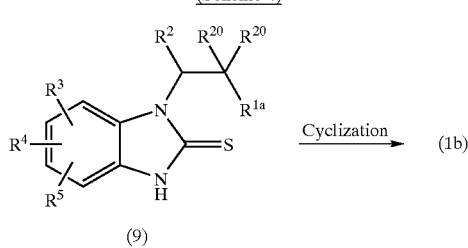

(In the above schemee, $R^{18}$ is a lower alkyl group, $R^{19}$ is a lower alkyl group or a lower alkyl-O— group, $R^{1a}$ is $R^1$, $COOR^{17}$ or hydrogen, $R^{20}$ is —O—$R^{21}$ or oxo group by integrating two, $R^{21}$ is a lower alkyl group, each of $X^1$ and $X^2$ is a halo, and $R^1$ to $R^5$, $R^{4a}$ and $R^{17}$ are as defined in the foregoing.)

The scheme 1, scheme 2, scheme 3 and scheme 4 are the production method of thiazolo[3,2-a]benzoimidazole ring. In the steps of from (2a) to (3a, 4a) in the scheme 1, (2a) and (6a) are allowed to react with each other in an alcohol solvent such as EtOH or MeOH or in an inert solvent such as THF, DMF, acetone or acetonitrile, in the presence of a base such as NaOH, KOH, NaH, $K_2CO_3$, $NaHCO_3$ or the (Scheme 5)

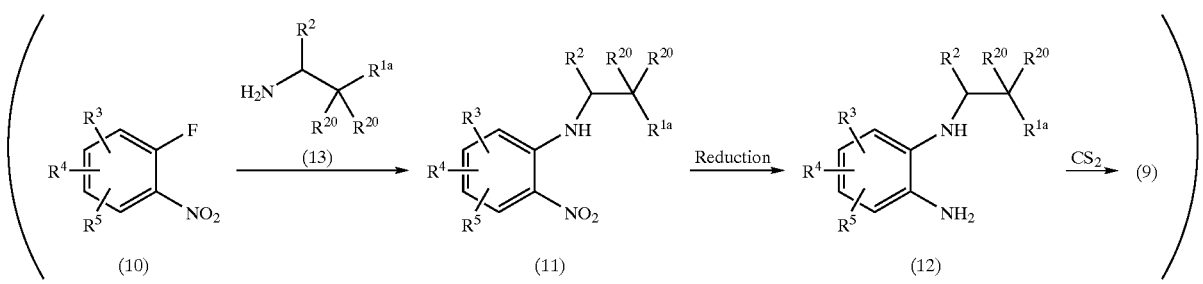

like, or under a neutral condition, at room temperature or under a heated condition. Also, in the steps of from (3a, 4a) to (1b), the (3a, 4a) is allowed to react with an acid halide (8) or an acid anhydride or mixed anhydride (7) in the presence of a base such as Py, TEA or NaOAc under an ice-cooled to heated condition, thereby obtaining (5) which is then subjected to the reaction in the presence of a base such as Py or the like in an inert solvent such as DMF or acetonitrile under a heated condition. Also, in the scheme 2, (2a) and (6b) are allowed to react with each other in the same manner as the case of the scheme 1, thereby obtaining (3b, 4b) which are then subjected to the reaction under an ice-cooling to heating condition in an acid such as concentrated sulfuric acid, trifluoroacetic acid or acetic acid or in a solvent such as Tol or $CCl_4$ using the aforementioned acid catalyst such as concentrated sulfuric acid or a Lewis acid catalyst such as $BF_3$—$Et_2O$. In this connection, in the production methods shown in the scheme 1 and scheme 2, the formed (1b) exists in position isomer forms in some cases depending on the substituents ($R^3$, $R^4$, $R^5$) but it is possible to produce respective position isomers selectively, for example by using the method shown in the schemee 3 and 4. That is, as shown in the scheme 3, (4c) or (4d) can be obtained as respective crystals by allowing (2a) and (6b) to react with each other like the case of the scheme 2 to obtain an equilibrium mixture (3c, 4c, 4d) and then crystallizing it under an appropriate precipitation condition. Also, it is possible to obtain (1c) or (1d) position-selectively by allowing (4c) or (4d) to undergo the reaction under an appropriate condition, e.g., at room temperature or under heating in concentrated sulfuric acid. Also, as shown in the scheme 4, (1b) can be produced position-selectively, e.g., by allowing the compound (9) produced by the method shown in the scheme 5 to undergo the reaction under an ice-cooling to heating condition using the aforementioned acid catalyst such as concentrated sulfuric acid or a Lewis acid catalyst such as $BF_3$—$Et_2O$ in an acid such as concentrated sulfuric acid, trifluoroacetic acid or acetic acid or in a solvent such as Tol or $CCl_4$.

(Second Production Method: Acylation of thiazolo[3,2-a] benzoimidazole Ring)

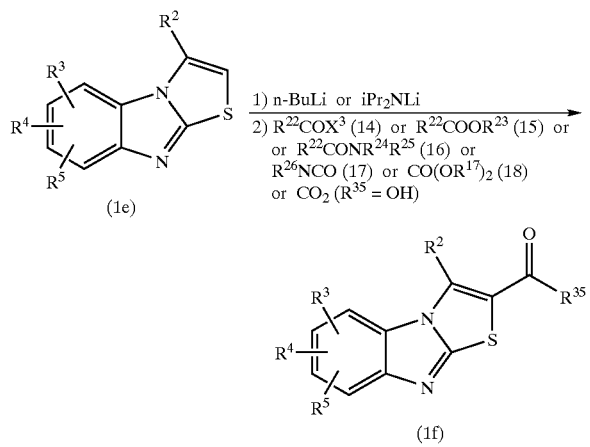

(In the above scheme, $R^{35}$ is $R^{22}$, —$OR^{17}$, —NH—$R^{26}$ or hydroxy group, $R^{22}$ is —$A^2$—$R^8$, $R^{23}$ is a lower alkyl group or alkali metal atom (e.g., Li, Na or the like), $R^{24}$ and $R^{25}$ are the same or different lower alkyl or one of them is lower alkyl-O— group, $R^{26}$ is $R^6$ or $R^7$, $X^3$ is a halo, and $R^2$ to $R^8$, $R^{17}$ and $A^2$ are as defined in the foregoing.)

In the scheme 6, (1e) is metallized using an organic metal reagent (e.g., BuLi, $iPr_2NLi$ or the like) in an inert solvent (e.g., THF, $Et_2O$ or the like) at a low temperature, preferably −78° C., and the product is allowed to react with corresponding acid halide (14), ester (15), amide (16), isocyanate (17), carbonic acid ester (18) or carbon dioxide at the same temperature to room temperature.

In the production methods in and after the third production method, the presence, position and kind of substituents other than the substituents of interest are applied only when they do not exert influences upon these production methods, so that the other substituents are omitted and only the substituents of interest are described.

(Third Production Method: Amidation)

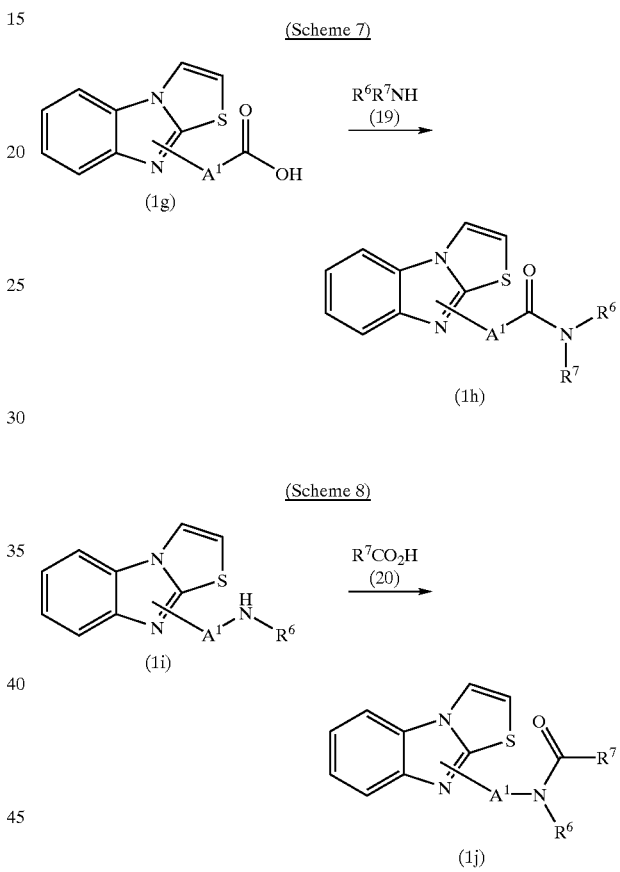

(In the above schemes, $R^6$, $R^7$ and $A^1$ are as defined in the foregoing.)

The scheme 7 and scheme 8 are usual amidation reactions. The reaction is carried out by converting a carboxylic acid into an acid chloride using a halogenation agent such as $SOCl_2$ or $(COCl)_2$ and then allowing the salt to undergo the reaction at ice-cooling to room temperature, or if necessary under a heating condition, in the presence of a corresponding primary or secondary amine and an organic base such as TEA or Py or an inorganic base such as $NaHCO_3$ or $K_2CO_3$, in an inert solvent such as DCE, $CH_2Cl_2$, $CHCl_3$ or 1,4-dioxane or in a two layer system solvent thereof with water, or using a base such as Py itself as the solvent. In addition to this, a usually used method can also be used, such as a method in which the carboxylic acid is made into a mixed acid anhydride and then allowed to react with an amine, a method in which $POCl_3$ is used as a condensing agent in Py solvent or a method in which amidation is directly carried out in the presence of an appropriate condensing agent such as diphenylphosphorylazide (to be referred to as DPPA hereinafter) or 1,1'-carbonylbis-1H-imidazole (to be referred to as CDI hereinafter).
(Fourth Production Method: Alkoxycarbonylation)

(Scheme 9)

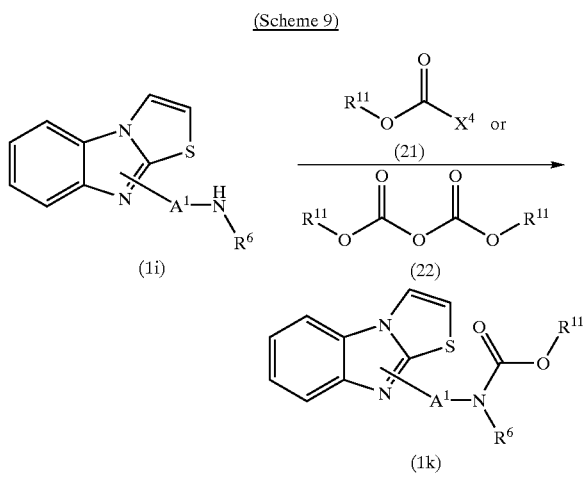

(In the above scheme, $X^4$ is a halo, and $R^6$, $R^{11}$ and $A^1$ are as defined in the foregoing.)

The scheme 9 is a method for the synthesis of a carbamic acid ester, and amine (1i) is allowed to react with (21) or (22) under ice-cooling to heating in an inert solvent (e.g. DCE, $CH_2Cl_2$, $CHCl_3$, THF, DMF or the like) in the presence of a base (e.g., TEA, 4-(N,N-dimethylamino)pyridine (DMAP), Py or the like), or under a neutral condition.
(Fifth Production Method: Esterification)

(Scheme 10)

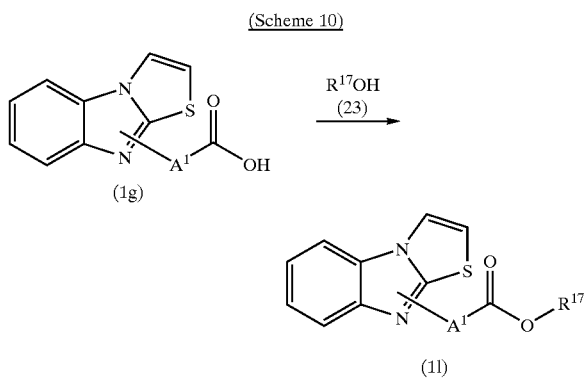

(In the scheme, $R^{17}$ and $A^1$ are as defined in the foregoing.)

The scheme 10 is a usual esterification reaction. The reaction is carried out with a corresponding alcohol (23), or using (23) itself as the solvent, in an inert solvent (e.g., Tol, THF or the like) in the presence of a catalyst such as concentrated sulfuric acid, concentrated hydrochloric acid, p-toluenesulfonic acid or the like at room temperature to heating condition, while dehydrating using a molecular sieve or Dean-Stark dehydration apparatus as occasion demands, or the carboxylic acid (1 g) is allowed to react with a corresponding alkyl halide under an ice-cooling to heating condition in an inert solvent (e.g., DMF, THF or the like) in the presence of a base (e.g., NaH, $K_2CO_3$ or the like). Alternatively, $SOCl_2$ is added dropwise to an alcohol (23) solution of (1 g) under ice-cooling, and the reaction is further carried out under a heating condition as occasion demands, or (1 g) is converted into an acid chloride or active ester and then allowed to react with (23).

(Sixth Production Method: Curtius Rearrangement)

(Scheme 11)

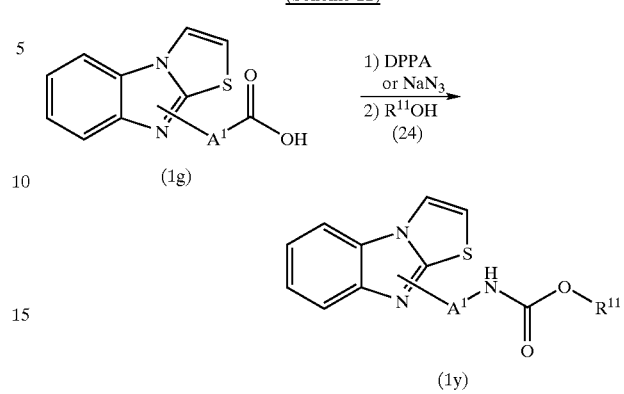

(In the above scheme, $R^{11}$ and $A^1$ are as defined in the foregoing.)

The scheme 11 is Curtius rearrangement. The reaction is carried out by converting the carboxylic acid (1 g) into an acid azide under a usual acid azide producing condition, illustratively a method in which the carboxylic acid is allowed to react with an azide forming agent such as DPPA or the like at ice-cooling to room temperature in an inert solvent (e.g., DMF or the like) or a method in which the carboxylic acid is converted into an acid halide, active ester or acid anhydride and then allowed to react with an azide forming agent (e.g., $NaN_3$ or the like), and then the reaction is carried out under a heating condition in the presence of a corresponding alcohol (24) in an inert solvent (e.g., DMF, Tol, THF or the like), or using the reacting alcohol (24) itself as the solvent.

(Seventh Production Method: Reduction by Metal Hydride)

(Scheme 12)

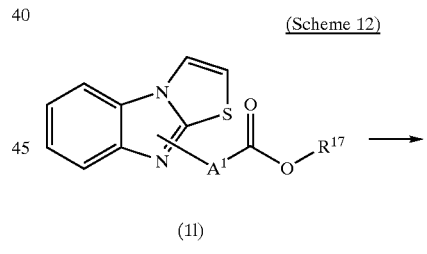

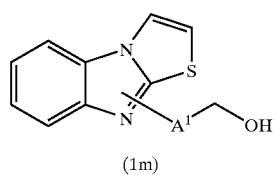

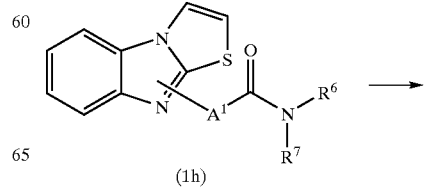

(Scheme 13)

(Eighth Production Method: Hydrolysis)

(Scheme 15)

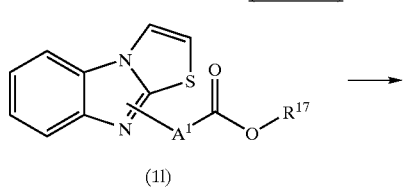

(1l)

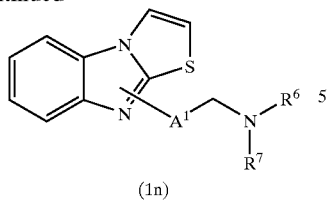

(1n)

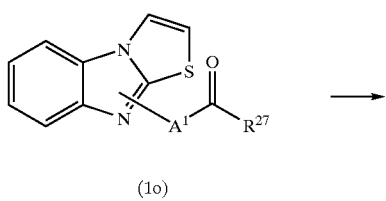

(Scheme 14)

(1o)

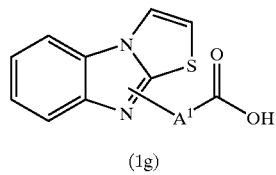

(1g)

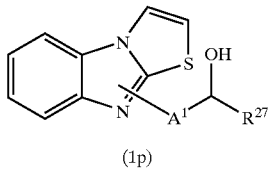

(1p)

(Scheme 16)

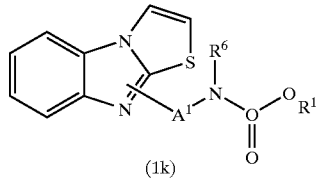

(1k)

(In the above schemes, $R^{27}$ is hydrogen or a lower alkyl group which may have a substituent, and $R^6$, $R^7$, $R^{17}$ and $A^1$ are as defined in the foregoing.)

The schemes 12 to 14 are reduction reactions by a metal hydride. When $R^{17}$ in the scheme 12 is hydrogen, the carboxylic acid (1i) is allowed to undergo the reaction under cooling to heating condition using $BH_3$ or a complex thereof in an inert solvent (e.g., THF, $Et_2O$ or the like), or (1i) is converted into an acid halide using a halogenation agent (e.g., $SOCl_2$, $(COCl)_2$ or the like) or into an active ester using a condensing agent (e.g., CDI or the like), and then allowed to undergo the reaction under ice-cooling or, as occasion demands, under a heating condition, in the aforementioned inert solvent or a mixed solvent thereof with water using a reducing agent (e.g., $NaBH_4$, $LiBH_4$, $LiAlH_4$, $(iBu)_2AlH$ or the like). Also, when $R^{17}$ in the scheme 12 is a lower alkyl group, the ester (1i) is allowed to undergo the reaction in an inert solvent (e.g., THF, $Et_2O$ or the like) or a mixed solvent thereof with EtOH, MeOH or the like, using the aforementioned reducing agent at −78° C. to room temperature, or under a heating condition as occasion demands. In the scheme 13, reaction of the amide (1h) is carried out using a reducing agent such as a complex (e.g., $LiAlH_4$, $(iBu)_2AlH$ or $BH_3$ or $BH_3$—$Me_2S$ or the like), in the aforementioned inert solvent under an ice-cooling to heating condition. In the scheme 14, reaction of the aldehyde (1o) is carried out using a reducing agent (e.g., $LiBH_4$, $NaBH_4$, $LiAlH_4$, $(iBu)_2AlH$ or the like) at −78° C. to room temperature in the aforementioned inert solvent, an alcohol or water.

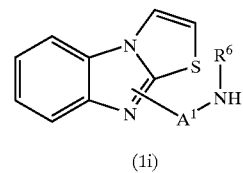

(1i)

(Scheme 17)

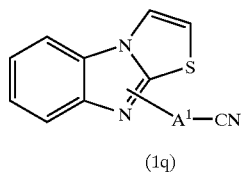

(1q)

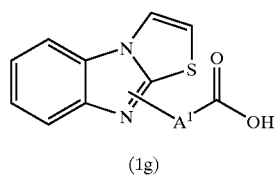

(1g)

(Scheme 18)

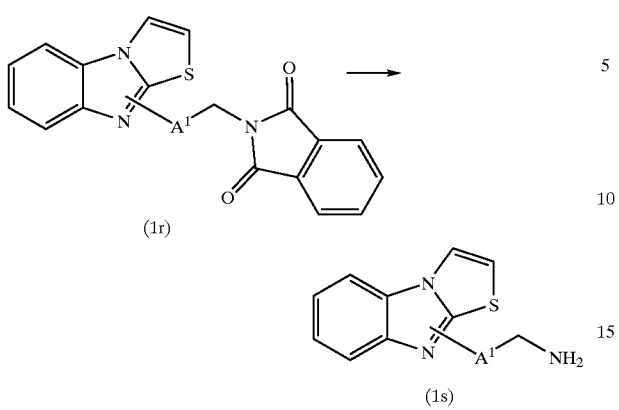

(In the above schemes, $R^5$, $R^{11}$, $R^{17}$ and $A^1$ are as defined in the foregoing.)

The schemes 15 to 18 are alkali or acid hydrolysis. That is, the reaction is carried out at room temperature or under a heating condition in a solvent such as MeOH, EtOH, THF, 1,4-dioxane, EtOAc or water or in a mixed solvent thereof, using NaOH, KOH, $K_2CO_3$ or the like in the case of alkali hydrolysis or hydrazine, methyl amine or the like in the case of the scheme 18, or using sulfuric acid, hydrochloric acid, nitric acid, TFA or the like in the case of acid hydrolysis.

(Ninth Production Method: O-Alkylation)

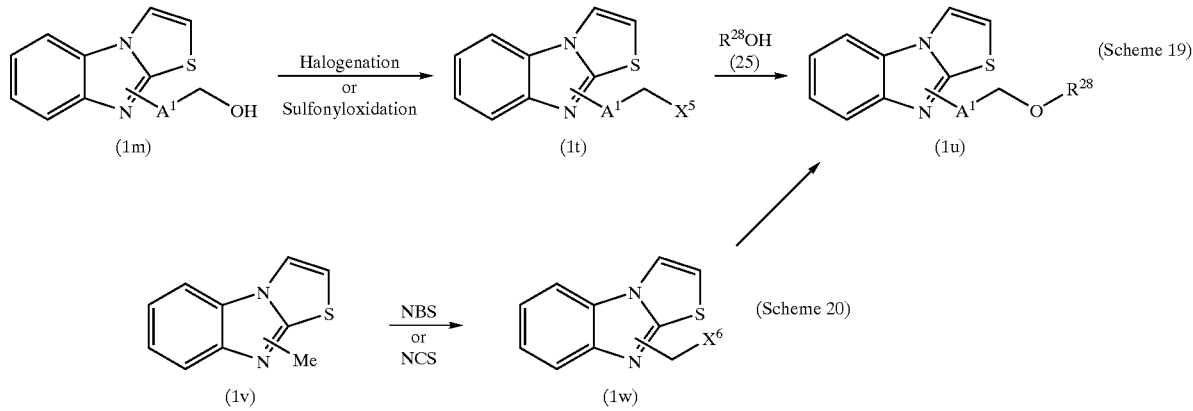

(In the above schemes, $R^{28}$ is —$A^2$—$R^9$, $X^5$ is a halo or sulfonyloxy group, $X^6$ is a halo and $R^9$, $A^2$ and $A^1$ are as defined in the foregoing, with the proviso that $A^1$ does not have hydroxy group in the schemes 19 and 20.)

The scheme 19 is halogenation or sulfonyloxy formation of alcohol and subsequent O-alkylation reaction. When $X^5$ in the scheme 19 is a halo, (1m) of the steps of from (1m) to (1t) is allowed to undergo the reaction under an ice-cooling to heating condition using a halogenation agent (e.g., $SOCl_2$, $(COCl)_2$ or the like) in an inert solvent (e.g., THF, 1,4-dioxane, $CH_2Cl_2$, $CCl_4$ or the like), or using the halogenation agent itself as the solvent. Also, when $X^5$ is sulfonyloxy, the reaction is carried out in the aforementioned inert solvent under an ice-cooling to room temperature condition in the presence of a base (e.g., TEA, Py or the like), using a sulfonyl forming agent (e.g., methanesulfonyl chloride, p-toluenesulfonyl chloride or the like). Also, when $A^1$ is a bond and $X^5$ is a halo in (1t), as shown in the scheme 20, (1v) can be converted into (1w) by carrying out the reaction under a heating condition using a halogenation agent (e.g., N-bromosuccinimide (NBS), N-chlorosuccinimide (NCS) or the like), in an inert solvent (e.g., $CCl_4$, $CHCl_3$ or the like) in the presence of a catalytically effective amount of a radical initiator (e.g., 2,2'-azobisisobutyronitrile (AIBN), dibenzoyl peroxide or the like). In the subsequent step of (1t) or (1w) to (1u), the reaction with an alcohol (25) is carried out under an ice-cooling to heating condition in an inert solvent (e.g., DMF, DMSO, THF, acetone, acetonitrile or the like) using a base (e.g., NaH, KOH, NaOH, $K_2CO_3$ or the like).

(Tenth Production Method: N-Alkylation)

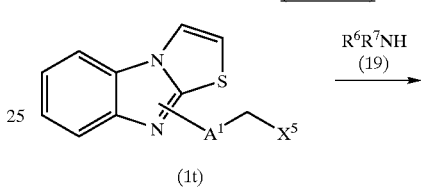

-continued

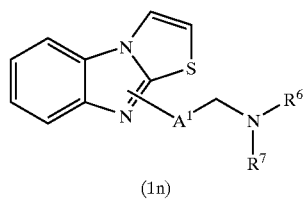

(Scheme 22)

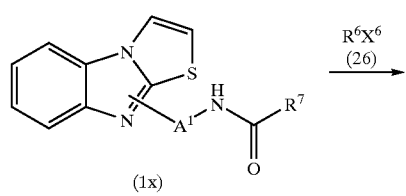

(Scheme 25)

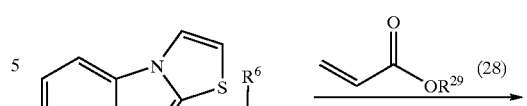

(Scheme 23)

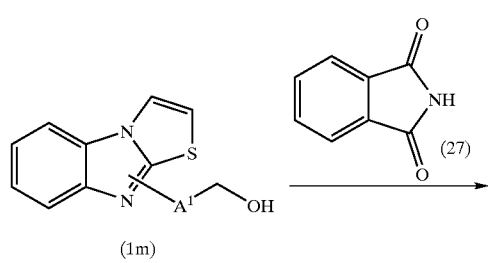

(Scheme 26)

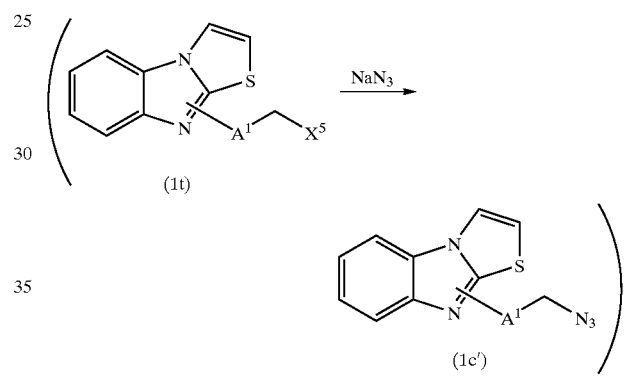

(Scheme 24)

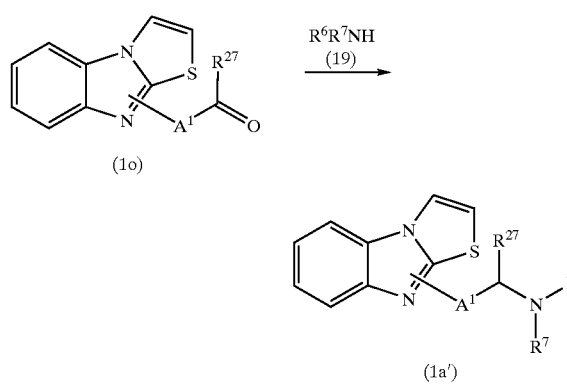

(In the above schemes, $R^{29}$ is a lower alkyl group, $X^6$ is a halo or sulfonyloxy, and $R^6$, $R^7$, $R^{27}$, $X^5$, and $A^1$ are as defined in the foregoing.)

The scheme 21 is N-alkylation reaction of amine, and the compound (1t) is allowed to react with an amine (19) under an ice-cooling to heating condition in an inert solvent (e.g., DMF, acetonitrile, acetone, $CH_2Cl_2$ or the like) in the presence of a base (e.g., $K_2CO_3$, $NaHCO_3$, TEA or the like), or using an excess amount of the amine (19) to be reacted. The scheme 22 is N-alkylation reaction of amide, and the compound (1x) is allowed to react with an alkylating agent (e.g., an alkyl halide, sulfonic acid alkyl ester (26) or the like) under an ice-cooling to heating condition in the presence of a base (e.g., NaH, $K_2CO_3$ or the like). The scheme 23 is Mitsunobu reaction in which an alcohol (1m) is allowed to react with an imide (27) under an ice-cooling to heating condition in an inert solvent (e.g., THF or the like) in the presence of an azodicarboxylic acid ester and $Ph_3P$. The scheme 24 is reductive amination reaction in which an aldehyde or ketone (1o) is allowed to react with an amine (19) under an ice-cooling to heating condition in a solvent (e.g., DCE, $CH_2Cl_2$, THF, MeOH or EtOH or the like), using a reducing agent (e.g., $NaB(Ac)_3H$, $NaB(CN)H_3$ or $NaBH_4$ or the like) in the presence of an acid catalyst (e.g., acetic acid, hydrochloric acid or the like) or a Lewis acid catalyst (e.g., Ti(OiPr)$_4$ or the like). The reaction can also be carried out under a usual catalytic reduction condition, instead of using the aforementioned reducing agent, illustratively in an atmosphere of hydrogen using a metal catalyst (e.g., Pd or the like). The scheme 26 is a Michael addition reaction in which an amine (1i) is allowed to react with an α,β-conjugated carbonyl (28) at room temperature or under a heating condition in a solvent (e.g., EtOH, MeOH or the like) in the presence of a base (e.g., NaOEt or the like), or under an acidic condition such as of acetic acid or under a neutral condition. Also, the azide compound (1c') can be produced by allowing (1t) to react with an azide forming agent (e.g., NaN$_3$ or the like).

(Eleventh Production Method: Nitration)

(Scheme 27)

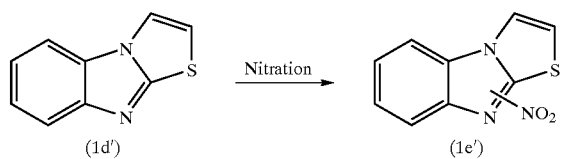

(1d')  (1e')

The scheme 27 is a nitration reaction. The reaction is carried out using nitric acid-sulfuric acid, nitric acid-acetic acid or nitric acid-acetic anhydride at ice-cooling to room temperature, or under a heating condition as occasion demands. Alternatively, it is carried out using a nitrating agent (e.g., NO$_2$—BF$_4$ or the like) as the nitrating agent in an inert solvent (e.g., Tol, acetonitrile, THF, sulfolane or the like) at ice-cooling to room temperature or under a heating condition as occasion demands.

(Twelfth Production Method: Reduction of Nitro Group or Azide)

(Scheme 28)

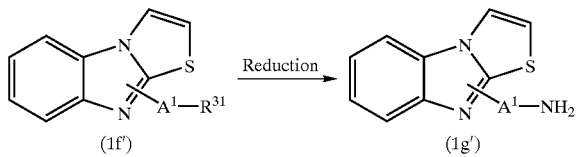

(1f')  (1g')

(In the above scheme, R$^{31}$ is nitro group or azido group, and A$^1$ is as defined in the foregoing.)

The scheme 28 is a reduction reaction of nitro group or azido group. The reaction is effected by carrying out catalytic reduction in an atmosphere of hydrogen or in the presence of a hydrogen donor such as ammonium formate, using a metal catalyst (e.g., Pd, Pt or the like), using Fe, SnCl$_2$ or the like in the presence of an acid such as acetic acid or hydrochloric acid when R$^{31}$ is nitro group or using a reducing agent (e.g., sodium hydrosulfite or the like) in a mixed solvent of water with MeOH, THF or the like under room temperature to heating condition.

(Thirteenth Production Method: Sandmeyer Reaction)

(Scheme 29)

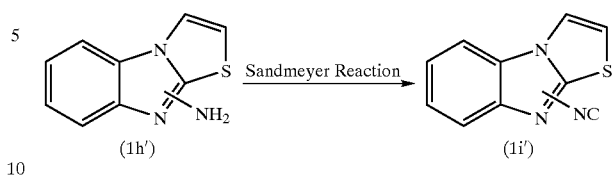

(1h')  (1i')

The scheme 29 is Sandmeyer reaction, and the reaction is carried out by allowing the aniline compound (1h') to react with a nitrite such as NaNO$_2$ in an aqueous solution such as of hydrochloric acid or sulfuric acid at an ice-cooling to room temperature, thereby forming a diazonium salt which is subsequently neutralized and then allowed to react with KCN, NaCN or a mixture thereof with CuCN in a mixed solvent of water with an organic solvent such as Tol at a ice-cooling to room temperature or under a heating condition as occasion demands.

(Fourteenth Production Method: Bromination of Aromatic Ring or Acetyl Group)

(Scheme 30)

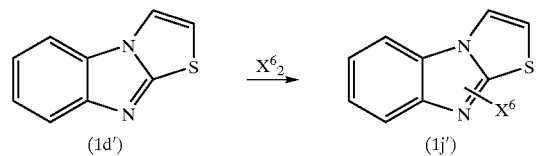

(1d')  (1j')

(Scheme 31)

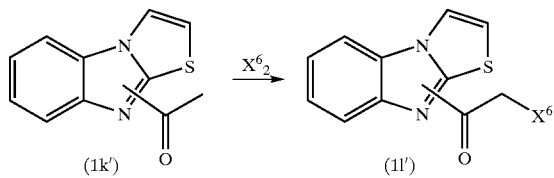

(1k')  (1l')

(In the above schemes, X$^6$ is Br or Cl.)

The schemes 30 and 31 are halogenation reaction. The reaction is carried out using bromine, an ammonium complex thereof or chlorine as a halogenation agent, by allowing the starting compound to react with bromine in a solvent (e.g., CCl$_4$, THF, MeOH or the like) at an ice-cooling to heating temperature, if necessary by adding concentrated hydrochloric acid.

(Fifteenth Production Method: Oxidation of Alcohol)

(Scheme 32)

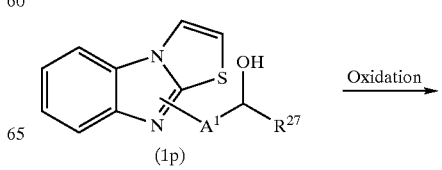

(1p)

-continued

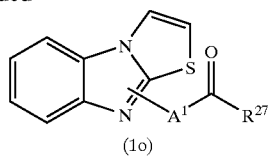

(1o)

(In the above scheme, $R^{27}$ and $A^1$ are as defined in the foregoing.)

The scheme 32 is an alcohol oxidation reaction. The reaction is carried out at a temperature of from $-78°$ C. to room temperature in an inert solvent such as $CH_2Cl_2$ using DMSO, $(COCl)_2$ or TEA, or under an ice-cooling to room temperature condition in DMSO solvent using $SO_3$—Py. In addition to the above, it can be produced by a usual oxidation reaction, illustratively, by oxidation with chromic acid, permanganic acid or the like.

(Sixteenth Production Method: Allylation of Amine)

(Scheme 33)

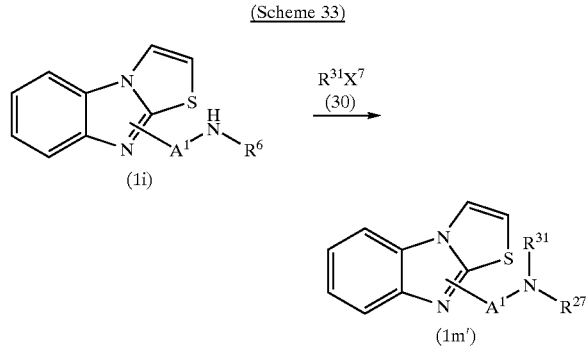

(In the above scheme, $R^{31}$ is an allyl group, $X^7$ is a halo or trifluoromethanesulfonyloxy group, and $R^6$ and $R^1$ are as defined in the foregoing.)

The scheme 33 is allylation reaction of amine, and the reaction is carried out by allowing the amine compound (1i) to react with an allyl halide or allyl trifurate (30) in an inert solvent such as DMF or without solvent in the presence or absence of a base such as $K_2CO_3$, or in the same manner in the presence of a catalyst such as Pd or Cu when the allyl trifurate has low activity.

(Seventeenth Production Method: O-Silylation of Alcohol)

(Scheme 34)

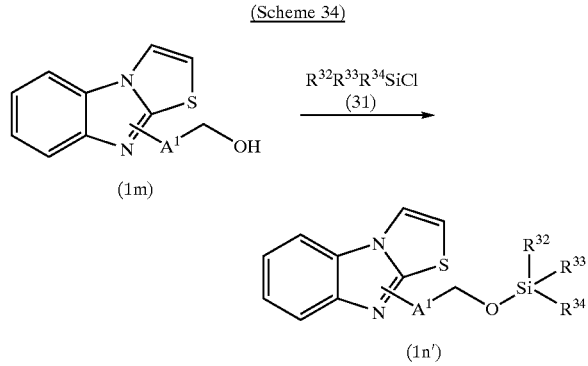

(In the above scheme, $R^{32}$ to $R^{34}$ may be the same or different from one another and each represents a lower alkyl group or phenyl group, and $A^1$ is as defined in the foregoing.)

The scheme 34 is a silylation reaction of alcohol, in which an alcohol (1m) is allowed to react with a silylation agent such as silane chloride (31) in an inert solvent (e.g., DCE, $CH_2Cl_2$, $CHCl_3$ or the like) in the presence of a base (e.g., imidazole, $Et_3N$, N,N-dimethyl-4-aminopyridine (DMAP), Py or the like), under ice-cooling to heating condition.

(Eighteenth Production Method: Desilylation of silyl ether)

(Scheme 35)

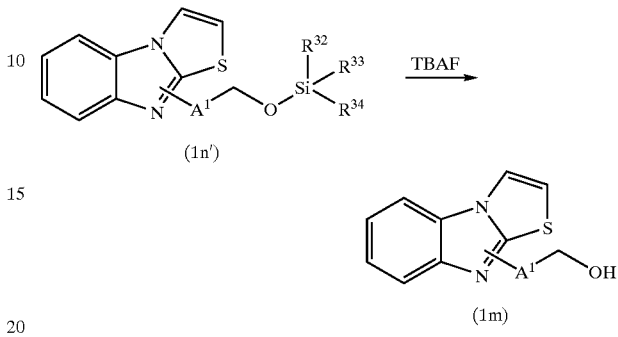

(In the above scheme, $R^{32}$ to $R^{34}$ and $A^1$ are as defined in the foregoing.)

The scheme 35 is a desilylation reaction of silyl ether, in which (1n') is allowed to react with a desilylation agent (e.g., KF, tetrabutylammonium fluoride (TBAF) or the like) at room temperature or under a heating condition in a solvent (e.g., THF, methanol or the like).

In this connection, the reaction schemes described in the above production methods are shown by typical structures, so that they are not restricted by the substituents of the formulae and can be broadly applied to a case in which a compound of the invention has similar substituents or a case in which a reaction substrate and a reactant have opposite relation.

The compound of the invention produced in this manner is isolated and purified in its free form or as a salt thereof.

The isolation and purification are carried out by employing usual chemical operations such as extraction, concentration, evaporation, crystallization, filtration, recrystallization and various types of chromatography.

Various isomers can be separated by selecting appropriate material compounds or making use of the difference in physicochemical properties among isomers. For example, optical isomers can be separated into stereochemically pure isomers by selecting an appropriate material or by a method for the optical resolution of racemic compounds (e.g., a method in which they are converted into diastereomer salts with a general optically active base and then subjected to optical resolution).

A pharmaceutical preparation which contains one or more of the compounds of the invention or salts thereof as an active ingredient is prepared using carriers, fillers and other additives generally used in the preparation of medicaments.

The carriers and fillers for pharmaceutical preparation use may be either solid or liquid, and their examples include lactose, magnesium stearate, starch, talc, gelatin, agar, pectin, acacia, olive oil, sesame oil, cacao butter, ethylene glycol and other generally used substances.

It may be administered either by oral administration through tablets, pills, capsules, granules, powders, solutions or the like, or by parenteral administration through injections such as for intravenous injection, intramuscular injection or the like, suppositories, percutaneous preparations and the like. Its dose is optionally decided by taking into consideration conditions of each case such as symptoms, age, sex and the like of the patient to be treated, but, usually, it is orally administered within the range of from 0.1 to 1,000 mg, preferably from 0.5 to 200 mg, per day per adult by dividing the daily dose into 1 to several doses per day or intravenously injected within the range of from 0.1 to 500 mg per day per adult by dividing the daily dose into 1 to several doses per day or continuously within the range of from 1 to 24 hours per day. As a matter of course, since the dose varies under various conditions as described in the foregoing, a smaller dose than the above range may be sufficient enough in some cases.

The solid composition for use in the oral administration according to the invention is used in the forms of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone, metasilicate or magnesium aluminate. In the usual way, the composition may contain other additives than the inert diluent, which include a lubricant such as magnesium stearate, a disintegrating agent such as calcium cellulose glycolate, a stabilizing agent such as lactose and a solubilization assisting agent such as glutamic acid or aspartic acid. If necessary, tablets or pills may be coated with a film of a gastric or enteric substance such as sucrose, gelatin, hydroxypropylcellulose or hydroxypropylmethylcellulose phthalate.

The liquid composition for oral administration use includes pharmaceutically acceptable emulsions, solutions, suspensions, syrups, elixirs and the like and contains a generally used inert diluent such as purified water or ethanol. In addition to the inert diluent, this composition may also contain auxiliary agents such as a moistening agent and a suspending agent, as well as a sweetener, a flavor, an aromatic and an antiseptic.

The injections for parenteral administration use include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil or the like), alcohol (e.g., ethanol or the like) and polysorbate 80. Such a composition may further contain auxiliary agents such as an antiseptic, a moistening agent, an emulsifying agent, a dispersing agent, a stabilizing agent (e.g., lactose) and a solubilization assisting agent (e.g., glutamic acid or aspartic acid). These compositions are sterilized by, e.g., filtration through a bacteria retaining filter, blending of a germicide or irradiation. Alternatively, they may be used by firstly making into sterile solid compositions and dissolving them in sterile water or a sterile solvent for injection use prior to their use.

BEST MODE FOR CARRYING OUT THE INVENTION

Next, the invention is described further in detail by examples, but the invention is not limited to these examples. In this connection, methods for producing material compounds used in Examples are described as Reference Examples. (The abbreviations used in the following are the same as those used in the production methods.)

Reference Example 1

Approximately 1:1 Mixture of ethyl 6-(t-butyldiphenylsilyloxy)methylthiazolo[3,2-a]benzoimidazole-2-carboxylate and ethyl 7-(t-butyldiphenylsilyloxymethyl)thiazolo[3,2-a]benzoimidazole-2-carboxylate Imidazole (24 g) and t-butyldiphenylsilyl chloride (96 g) were added to DMF (300 ml) solution of 5-hydroxymethyl-2-mercaptobenzoimidazole (60 g), and the mixture was stirred at room temperature for 2 hours. Next, this was mixed with MeOH (50 ml) and stirred and then mixed with water and diisopropyl ether and further stirred. The precipitate was collected by filtration and washed with water and diisopropyl ether to obtain 5-(t-butyldiphenylsilyloxymethyl)-2-mercaptobenzoimidazole (107 g). Next, 2-butanone (300 ml) solution of this compound (21 g) and ethyl 2-chloroacetoacetate (11 ml) was heated under reflux for 2 hours. The reaction mixture was concentrated under a reduced pressure, neutralized with saturated $NaHCO_3$ aqueous solution and then extracted with EtOAc and washed with water and saturated brine. After drying with anhydrous $MgSO_4$, the solvent was evaporated under a reduced pressure, and the resulting residue was purified by a silica gel column chromatography (to be referred to as column chromatography hereinafter) (eluent; n-hexane (to be referred to as Hex hereinafter):EtOAc=3:1–2:1), thereby obtaining ethyl 2-[(5-t-butyldiphenylsilyloxymethylbenzoimidazol-2-yl)thio]acetoacetate (23 g). Next, a DMF (300 ml) solution containing this compound, acetic acid formic acid anhydride (5.5 g) and Py (8.4 ml) was heated and stirred at 75° C. for 2 hours. The reaction mixture was concentrated under a reduced pressure while heating, diluted with EtOAc, washed with saturated $NaHCO_3$ aqueous solution, water and saturated brine and then dried with anhydrous $MgSO_4$, subsequently evaporating the solvent under a reduced pressure. The resulting residue was purified by a column chromatography (eluent; Hex:EtOAc=5:1–4:1) to obtain the title compound (16 g).

MS (FAB): 515 (M+1)

Reference Example 2

Approximately 1:1 Mixture of 6-(t-butyldiphenylsilyloxymethyl)thiazolo[3,2-a]benzoimidazole-2-carboxylic acid and 7-(t-butyldiphenylsilyloxymethyl)thiazolo[3,2-a]benzoimidazole-2-carboxylic acid An EtOH (160 ml) solution of the compound of Reference Example 1 (16 g) was mixed with 1 M NaOH aqueous solution (100 ml), and the mixture was stirred at room temperature for 30 minutes. The reaction solution was neutralized with 1 M HCl (100 ml) and then mixed with water (500 ml) and stirred. The resulting precipitate was collected by filtration, washed with water and then dried under a reduced pressure to obtain the title compound (14 g).

MS (FAB): 487 (M+1)

Reference Example 3

Approximately 1:1 Mixture of 6-t-butyldiphenylsilyloxymethyl-N-cyclohexyl-N-methylthiazolo[3,2-a]benzoimidazole-2-carboxamide and 7-t-butyldiphenylsilyloxymethyl-N-cyclohexyl-N-methylthiazolo[3,2-a]benzoimidazole-2-carboxamide At −20° C., $POCl_3$ (5.6 ml) was added to Py (150 ml) solution of the compound of Reference Example 2 (19 g) and N-methylcyclohexylamine (10.4 ml), and the mixture was stirred at the same temperature for 4 hours. The reaction mixture was poured into ice water and stirred, and then the resulting precipitate was collected by filtration, washed with water and dried under a reduced pressure to obtain the title compound (22 g).

MS (FAB): 582 (M+1)

Reference Example 4

2-Methyl hydrogen thiazolo[3,2-a]benzoimidazole-2,6-dicarboxylate sulfate

Methyl 2-chloro-3-hydroxypropenoate (114 g) was added to DMF (460 ml) solution of 2-mercaptobenzoimidazole-5-carboxylic acid (135 g), and the mixture was stirred overnight at 60° C. After cooling to room temperature, water (3 L) was gradually added to the reaction solution and stirred. The thus precipitated crystals were collected by filtration to obtain crude crystals of 2-methyl hydrogen 2,3-dihydro-3-hydroxythiazolo[3,2-a]benzoimidazole-2,7-dicarboxylate (168 g). Next, the thus obtained crude crystals were suspended in 1,4-dioxane (1.5 L), and the suspension was mixed with 4 M HCl 1,4-dioxane solution (500 ml) and stirred at room temperature for 60 hours. The resulting precipitate was collected by filtration and washed with 1,4-dioxane to obtain crude crystals of 2-methyl hydrogen 2,3-dihydro-3-hydroxythiazolo[3,2-a]benzoimidazole-2,6-dicarboxylate hydrochloride (189 g). The thus obtained crude crystals were slowly added to concentrated sulfuric acid (750 ml) which was heated at 60° C. and stirred at the same temperature for 1 hour. After cooling to room temperature, the reaction solution was poured into ice water, and the thus precipitated crystals were collected by filtration to obtain the title compound (152 g).

NMR (DMSO-$d_6$): δ9.51 (s, 1 H), 8.84 (s, 1 H), 8.01 (dd, 1 H), 7.75 (d, 1 H), 7.30–8.00 (br), 3.92 (s, 3 H).

Reference Example 5

Methyl 6-hydroxymethylthiazolo[3,2-a]benzoimidazole-2-carboxylate

CDI (65 g) was added to THF (500 ml) suspension of the compound of Reference Example 4 (50 g) and stirred at 60° C. for 2 hours. After cooling the reaction solution to −20° C., aqueous solution (200 ml) of $NaBH_4$ (30 g) was gradually added thereto, and the mixture was stirred under ice-cooling for 2 hours. At the same temperature, this was mixed with concentrated hydrochloric acid (200 ml) and water (200 ml) and further stirred overnight at room temperature. The reaction solution was neutralized with 20% NaOH aqueous solution, and the thus precipitated crystals were collected by filtration to obtain the title compound (25 g).

NMR (DMSO-$d_6$): δ9.42 (s, 1 H), 8.12 (s, 1 H), 7.65 (d, 1 H), 7.36 (d, 1 H), 5.33 (t, 1 H), 4.65 (d, 2 H), 3.91 (s, 3 H).

Reference Example 6

6-Hydroxymethylthiazolo[3,2-a]benzoimidazole-2-carboxylic acid

A MeOH (189 ml) solution of the compound of Reference Example 5 (33 g) was mixed with 1 M NaOH aqueous solution (189 ml), and the mixture was stirred at 50° C. for 2 hours. After ice-cooling, the reaction solution was mixed with 1 M HCl aqueous solution (189 ml), and the thus precipitated crystals were collected by filtration to obtain the title compound (31 g).

NMR (DMSO-$d_6$): δ9.27 (s, 1 H), 8.12 (brs, 1 H), 7.65 (d, 1 H), 7.36 (dd, 1 H), 4.65 (s, 2 H).

Reference Example 7

Ethyl thiazolo[3,2-a]benzoimidazole-2-carboxylate

Acetone (1.5 L) solution of 2-mercaptobenzoimidazole (150 g) and ethyl 2-chloroacetoacetate (247 g) was heated under reflux for 5 hours. The reaction solution was cooled to room temperature, and then the resulting precipitate was collected by filtration to obtain ethyl 2-[(benzoimidazol-2-yl)thio]acetoacetate hydrochloride (303 g) as colorless crystals. The thus obtained crystals (45 g) were dissolved in DMF (200 ml), and the solution was mixed with Py (32 ml) and acetic acid formic acid anhydride (35 g) and stirred for 3 hours while heating at 100° C. After cooling, the reaction solution was poured into water, and the resulting precipitate was collected by filtration and washed with water. The thus obtained solid was dried under a reduced pressure, purified by a column chromatography (eluent; $CHCl_3$) and then recrystallized from EtOAc/Hex to obtain the title compound (22 g).

MS (FAB): 247 (M+1)

Reference Example 8

Thiazolo[3,2-a]benzoimidazole-2-carboxylic acid

The compound of Reference Example 7 (4.3 g) was dissolved in a mixed solvent of THF (100 ml)/MeOH (200 ml), and the solution was mixed with 1 M NaOH aqueous solution (30 ml) and stirred at room temperature for 5 hours. After completion of the reaction, this was neutralized by adding 1 M HCl aqueous solution (30 ml), and the resulting precipitate was collected by filtration to obtain the title compound (2.8 g).

MS (FAB): 219 (M+1)

Reference Example 9

3-Methylthiazolo[3,2-a]benzoimidazole-2-carboxylic acid

This was produced from ethyl 3-methylthiazolo[3,2-a]benzoimidazole-2-carboxylate in the same manner as described in Reference Example 8. (*Can. J. Chem.*, 45 (23), 2903–2912 (1967)

Reference Example 10

6-Amino-N-cyclohexyl-N-methylthiazolo[3,2-a]benzoimidazole-2-carboxamide dihydrochloride The compound of Example 50 (12.5 g) was dissolved in a mixed solvent of THF (230 ml)/MeOH (120 ml), and the solution was mixed with aqueous solution (100 ml) of $Na_2S_2O_4$ (30.4 g) and heated under reflux for 3 hours. After cooling, the reaction solution was mixed with concentrated hydrochloric acid (30 ml) and again heated under reflux for 1 hour. The reaction solution was concentrated under a reduced pressure, diluted with water and then neutralized with NaOH. The resulting precipitate was collected by filtration, washed with water and then dried under a reduced pressure, and the thus obtained crude product was purified by a column chromatography (eluent; $CHCl_3$:MeOH=1:1) to obtain desalted form of the title compound (9.4 g). This was converted into hydrochloride in the usual way to obtain the title compound.

MS (FAB): 329 (M+1)

Reference Example 11

6-Amino-N-cyclohexyl-N,3-dimethylthiazolo[3,2-a]benzoimidazole-2-carboxamide dihydrochloride This was produced from the compound of 49 in the same manner as described in Reference Example 10. (WO/9944639)

Reference Example 12

2-Hydroxymethyl-3-methylthiazolo[3,2-a]benzoimidazole

Under ice-cooling, 3-methylthiazolo[3,2-a]benzoimidazole-2-carboxylic acid ethyl ester (*Can. J. Chem.*, 45 (23), 2903–2912 (1967) (10 g) was added to THF (250 ml) suspension of LiAlH$_4$ (1.46 g) and stirred at the same temperature for 1 hour. While cooling, the reaction solution was mixed with Na$_2$SO$_4$.10H$_2$O and stirred, and then the insoluble matter was removed by filtration and the solvent was evaporated under a reduced pressure to obtain the title compound (6.36 g).

MS (EI): 218 (M+)

Reference Example 13

3-Methylthiazolo[3,2-a]benzoimidazole

2-Mercaptobenzoimidazole (15.0 g) was added to EtOH (100 ml) solution of KOH (6.60 g), and the mixture was heated under reflux for 1 hour. After cooling to room temperature, this was mixed with 2-chloroacetone (7.96 ml) and stirred overnight. The reaction solution was mixed with EtOAc and stirred, the insoluble matter was removed by filtration and then the solvent was evaporated under a reduced pressure. The thus obtained oily material was dissolved in concentrated sulfuric acid (100 ml) and stirred at room temperature for 6 hours. The reaction solution was poured into ice water and then neutralized with 28% NH$_3$ aqueous solution, and the resulting precipitate was collected by filtration. This was recrystallized from MeOH to obtain the title compound (9.60 g) as light brown crystals. (*J. O. C.*, 29 (4), 865–9 (1964))

Reference Example 14

Ethyl(3-methylthiazolo[3,2-a]benzoimidazol-2-yl)acetate hydrochloride

Several drops of concentrated sulfuric acid was added to acetic acid (100 ml) solution of 2-mercaptobenzoimidazole (7.51 g) and ethyl levulinate (7.09 ml), and the mixture was heated under reflux for 20 hours. After cooling to room temperature, the thus precipitated material was removed by filtration and the solvent was evaporated under a reduced pressure. The resulting residue was neutralized with saturated NaHCO$_3$ aqueous solution, extracted with EtOAc, washed with water and saturated brine and dried with anhydrous Na$_2$SO$_4$, and then the solvent was evaporated under a reduced pressure. The resulting residue was purified by a column chromatography (eluent; Hex:EtOAc=2:1–1:1) and converted into hydrochloride in the usual way, thereby obtaining the title compound (949 mg).

MS (FAB): 275 (M+1)

Reference Example 15

(3-Methylthiazolo[3,2-a]benzoimidazol-2-yl)acetic acid

A MeOH (4 ml) solution of the compound of Reference Example 13 (120 mg) was mixed with 1 M NaOH aqueous solution (4 ml) and stirred at room temperature for 1 hour. After neutralization of the reaction solution with acetic acid, the resulting precipitate collected by filtration and washed with water and iPrOH to obtain the title compound (85 mg).

MS (FAB): 247 (M+1)

Structures and physical property values (mass spectrum) of the example compounds of the invention are shown in the following table.

Each abbreviation in the table means as follows.

Ex: example number, Me: methyl, Et: ethyl, cPen: cyclopentyl, cHex: cyclohexyl, cHept: cycloheptyl, neo-Pen: neopentyl, sec-But: secondary butyl, Sal: salt, Data: physical property value, M1: MS (FAB), M2: MS (EI), and inside [ ] shows synthesis method wherein Meth: production method disclosed in the specification, EX: Example, Ref: Reference Example and Side-Pro: by-product.

TABLE 1

Example I

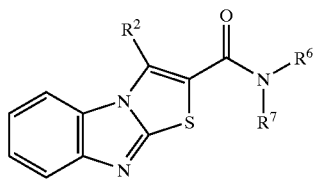

| Ex | R$^2$ | R$^6$ | R$^7$ | salt | DATA |
|---|---|---|---|---|---|
| 1 | Me | Me | H | — | m.p.: 248–249° C.[Ref9→Meth3] |
| 2 | Me | Et | Pr | HCl | m.p.: 141.5–144° C.[Ref9→Meth3] |
| 3 | H | cHex | Me | — | M1: 314(M+1) |
| 4 | Me | cHex | Me | HCl | M2: 327(M+)[Ref9→Meth3] |
| 5 | H | 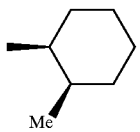 | Me | HCl | M1: 314(M+)[Ref8→Meth3] |

TABLE 1-continued

| Ex | | Structural Formula | | salt | DATA |
|---|---|---|---|---|---|
| 6 | H | (bicyclic structure) | H | — | M1: 312(M+1)[Ref8→Meth3] |
| 7 | Me | (adamantyl) | H | — | M1: 366(M+1)[Ref9→Meth3] |
| 8 | Me | CH2-cHept | Me | HCl | M1: 356(M+1)[Ref9→Meth3] |
| 9 | H | (ethyl-methyl-cyclopropyl) | Me | — | M1: 300(M+1)[Ref8→Meth3] |
| 10 | Me | (N-methylmorpholinyl) in combination | | (CO2H)2 | m.p.: 148.5–150° C.[Ref9→Meth3] |
| 11 | H | (N-methyl octahydroindolyl) in combination | | — | M1: 326(M+1)[Ref8→Meth3] |
| 12 | H | (N-methyl azaspiro) in combination | | — | M1: 340(M+1)[Ref8→Meth3] |
| 13 | H | (trans-2-aminocyclohexyl) | H | 2HCl | M1: 315(M+1)[Ref8→Meth3] |
| 14 | H | (tetrahydropyranyl) | Me | HCl | M1: 316(M+1)[Ref8→Meth3] |
| 15 | H | 1-piperidinyl | Me | 2HCl | M1: 315(M+1)[Ref8→Meth3] |
| 16 | H | cHex | NH2 | HCl | M1: 315(M+1)[Ex17→Meth8] |
| 17 | H | cHex | NHBoc | — | M1: 415(M+1)[Ref8→Meth3] |
| 18 | H | cHex | (CH2)3NH2 | 2HCl | M1: 357(M+1)[Ex19→Meth8] |
| 19 | H | cHex | (CH2)3NHBoc | — | M1: 457(M+1)[Ref8→Meth3] |
| 20 | H | cHex | (CH2)3NMe2 | 2HCl | M1: 371(M+1)[Ex18→Ex88] |
| 21 | Me | CH2CO2Me | H | HCl | m.p.: 193.5–194.5° C.[Ref9→Meth3] |
| 22 | Me | (CH2)2CO2Me | H | HCl | m.p.: 153–154° C.[Ref9→Meth3] |
| 23 | Me | 4-pyridyl | H | 2HCl | M1: 309(M+1)[Ref9→Meth3] |
| 24 | Me | (N-methyl tetrahydroquinolinyl) in combination | | HCl | M2: 347(M+)[Ref9→Meth3] |

TABLE 1-continued

| 25 | [structure: 3-methyl-benzimidazothiazole with CH2-C(=O)-piperidine] | | | | | HCl | M1: 314(M+1)[Ref15→Meth3] |

Example II

[structure: benzimidazothiazole core with R² at 3-position, Rᵃ, Rᵇ, Rᶜ, Rᵈ on benzene ring, and C(=O)N(CH₃)(cyclohexyl) carboxamide at 2-position]

| Ex | R² | Rᵃ | Rᵇ | Rᶜ | Rᵈ | salt | DATA |
| --- | --- | --- | --- | --- | --- | --- | --- |
| 26 | Me | H | N(Me)2 | H | H | HCl | M1: 371(M+1)[Ref11→Ex88] |
| 27 | Me | H | NH(iPr) | H | H | 2HCl | M1: 385(M+1)[Ref11→Meth10] |
| 28 | Me | H | NH(Bn) | H | H | HCl | M1: 433(M+1)[Ref11→Meth10] |
| 29 | Me | H | N(Bn)2 | H | H | HCl | M1: 523(M+1)[Ex28 side-pro] |
| 30 | Me | H | —NH-CH2-(3-pyridyl) | H | H | 2HCl | M1: 434(M+1)[Ref11→Meth10] |
| 31 | Me | H | NH(CH2CO2Et) | H | H | HCl | M1: 429(M+1)[Ref11→Meth10] |
| 32 | Me | H | NH[(CH2)2CO2Me] | H | H | 2HCl | M1: 429(M+1)[Ref11→Meth10] |
| 33 | Me | H | NH[(CH2)2OH] | H | H | 2HCl | M1: 387(M+1)[Ex31→Meth7] |
| 34 | Me | H | NH[(CH2)3OH] | H | H | 2HCl | M1: 401(M+1)[Ex32→Meth7] |
| 35 | Me | H | —NH-(CH2)2-phthalimide | H | H | — | M1: 516(M+1)[Ref11→Meth10] |
| 36 | Me | H | NH[(CH2)2NH2] | H | H | HCl | M1: 386(M+1)[Ex35→Meth8] |
| 37 | Me | H | —NH-(1-methyl-piperidin-4-yl) | H | H | HCl | M1: 440(M+1)[Ref11→Meth10] |
| 38 | H | H | —NH-(2-pyridyl) | H | H | 2HCl | M1: 406(M+1)[Ref10→Meth16] |
| 39 | Me | H | NH(COMe) | H | H | HCl | M1: 385(M+1)[Ref11→Meth3] |
| 40 | Me | H | NH(COCH2NHCO2t-Bu) | H | H | — | M1: 500(M+1)[Ref11→Meth3] |
| 41 | H | H | NH(COCH2NH2) | H | H | 2HCl | M1: 386(M+1) |
| 42 | Me | H | NH[CO(CH2)2NH2] | H | H | 2HCl | M1: 414(M+1)[Ref11→Ex41] |
| 43 | Me | H | NH[CO(CH2)2NMe2] | H | H | 2HCl | M1: 442(M+1)[Ex42→Ex88] |
| 44 | H | H | NH(COCF3) | H | H | CF3CO2H | M1: 425(M+1)[Ref10→Meth3] |
| 45 | H | H | NH[CO(CH2)2Cl] | H | H | — | M1: 435(M+1)[Ref10→Meth4] |
| 46 | Me | H | NH(CO2t-Bu) | H | H | — | M1: 443(M+1)[Ref10→Meth4] |
| 47 | Me | H | N(Me)(CO2t-Bu) | H | H | — | M1: 457(M+1)[Ex46→Meth10] |
| 48 | H | H | —N-(2-oxo-oxazolidin-3-yl) | H | H | — | M1: 399(M+1)[Ex45→Meth10] |

TABLE 1-continued

| | | | | | | | |
|---|---|---|---|---|---|---|---|
| 49 | Me | H | NO2 | H | H | — | M1: 373(M+1)[Ex4→Meth11] |
| 50 | H | H | NO2 | H | H | — | M1: 359(M+1) |
| 51 | Me | H | OMe | H | H | HCl | M1: 358(M+1)[Meth1,8,3] |
| 52 | Me | H | CN | H | H | — | M1: 353(M+1)[Ref11→Meth13] |
| 53 | Me | H | Br | H | H | — | M1: 406(M+)408(M+2) [Ex4→Meth14] |
| 54 | Me | H | CO2H | H | H | — | M1: 371(M+)[Ex52→Meth8] |
| 55 | Me | H | CO2Me | H | H | — | M1: 386(M+1)[Ex54→Meth5] |
| 56 | H | H | H | H | Me | — | M1: 328(M+1)[Meth1,8,3] |
| 57 | H | CH2OH | NMe2 | H | H | 2HCl | M1: 387(M+1)[Ref10→Ex88] |
| 58 | CH2Br | H | H | H | H | — | M1: 406(M+)408(M+2) [Ex4→Meth9] |
| 59 | CH2NHMe | H | H | H | H | 2HCl | M1: 357(M+1)[Ex58→Meth10] |
| 60 | CH2N(Me)2 | H | H | H | H | 2HCl | M1: 371(M+1)[Ex58→Meth10] |
| 61 | CH2OMe | H | H | H | H | — | M1: 358(M+1)[Ex58→Meth9] |
| 62 | CF3 | H | H | H | H | — | M1: 382(M+1)[Meth1,8,3] |

Example III

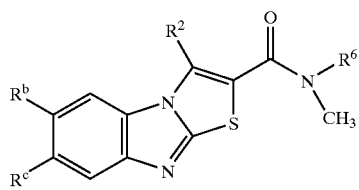

| Ex | $R^2$ | $R^6$ | $R^b$ | $R^c$ | salt | Data |
|---|---|---|---|---|---|---|
| 75 | H | neo-Pen | ⌇N(H)CH2CH2OMe | H | 2HCl | M1: 389(M+1) |
| 76 | H | cHex | CH$_2$NMe$_2$ | H | 2HCl | M1: 371(M+1)[Ex63→Ex75] |
| 77 | H | cHex | CH$_2$NH(Et) | H | 2HCl | M1: 371(M+1)[Ex63→Ex75] |
| 78 | H | cHex | CH2-piperidinyl | H | 2HCl | M1: 411(M+1)[Ex63→Ex75] |
| 79 | H | cHex | CH2N(Me)CH2CH2OH | H | 2HCl | M1: 401(M+1)[Ex63→Ex75] |
| 80 | H | cHex | CH2NHCH2CH2OMe | H | 2HCl | M1: 401(M+1)[Ex63→Ex75] |
| 81 | H | neo-Pen | CH2NHCH2CH2CH2OMe | H | 2HCl | M1: 403(M+1)[Ex64→Ex75] |
| 82 | H | cHex | CH2NHCH2CH2NMe2 | H | 3HCl | M1: 414(M+1)[Ex63→Ex75] |
| 83 | H | cHex | CH2-morpholinyl | H | 2HCl | M1: 413(M+1)[Ex63→Ex75] |
| 84 | H | cHex | H | CH2-morpholinyl | 2HCl | M1: 413(M+1)[Ex65→Ex75] |
| 85 | H | cHex | CH2-imidazolyl | H | 2HCl | M1: 394(M+1)[Ex63→Ex75] |

TABLE 1-continued

| Ex | | | | | salt | DATA |
|---|---|---|---|---|---|---|
| 86 | Me | cHex | (1-ethylpyrazol-3-yl) | H | HCl | M1: 394(M+1)[Ex63→Ex75] |
| 87 | H | cHex | -CH2CH2N(Me)CH2C(O)OMe | H | 2HCl | M1: 429(M+1)[Ex63→Ex75] |
| 88 | H | neo-Pen | -CH2CH2N(Me)CH2CH2OMe | H | 1.5C4H4O4 | M1: 403(M+1) |
| 89 | H | cHex | -CH2CH2N(Me)CH2CH2OMe | H | 1.5C4H4O4 | M1: 415(M+1) |
| 90 | H | cHex | -CH2CH2N(Me)CH2C(O)OH | H | 2HCl | M1: 415(M+1) |

Example IV

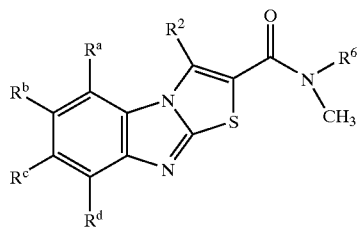

| Ex | Rª | Rᵇ | Rᶜ | Rᵈ | R⁶ | salt | DATA |
|---|---|---|---|---|---|---|---|
| 63 | H | CH2OH | H | H | cHex | HCl | M1: 344(M+1) |
| 64 | H | CH2OH | H | H | neo-Pen | HCl | M1: 332(M+1) |
| 65 | H | H | CH2OH | H | cHex | HCl | M1: 344(M+1) |
| 66 | H | CHO | H | H | cHex | — | M1: 342(M+1) |
| 67 | H | CHO | H | H | neo-Pen | — | M1: 330(M+1) |
| 68 | H | H | H | CH2OH | cHex | — | M1: 344(M+1) |
| 69 | H | H | H | CH2OAc | cHex | HCl | M1: 386(M+1) |
| 70 | H | H | CHO | H | cHex | — | M1: 342(M+1)[Ex65→Ex69] |
| 71 | H | CH2CHO | H | H | neo-Pen | — | NMR(CDCl3)9.82(t,1H) |
| 72 | H | -CH2CH2CH2NHCH2CH2OMe | H | H | neo-Pen | 2HCl | M1: 403(M+1) |
| 73 | H | H | 2-(1-hydroxyethyl)-1H-imidazol-2-yl | H | cHex | 2HCl | M1: 410(M+1) |
| 74 | H | CH2N3 | H | H | cHex | — | M1: 369(M+1) |

Example V

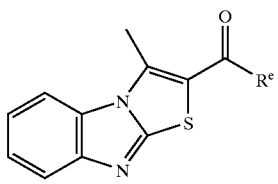

| Ex | Rᵉ | salt | DATA |
|---|---|---|---|

TABLE 1-continued
| Ex | Rᵉ | | salt | DATA |
|---|---|---|---|---|
| 91 | 138 | 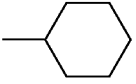 | HCl | M2: 298(M+) |
| 92 | 157 | 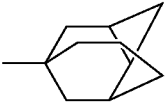 | HCl | M1: 351(M+1)[Ref13→Meth2] |
| Ex | Rᵉ | salt | DATA |
|---|---|---|---|
| 93 | 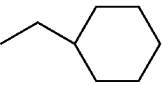 | — | M2: 312(M+)[Ref13→Meth2] |
| 94 | 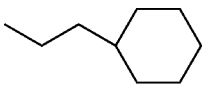 | — | M1: 327(M+1)[Ref13→Meth2] |
| 95 | 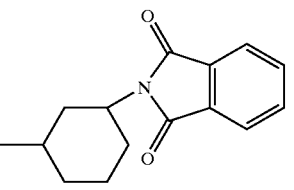 | — | M1: 444(M+1)[Ref13→Meth2] |
| 96 | 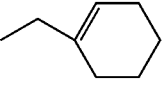 | — | M1: 311(M+1)[Ex97 side-pro] |
| 97 | 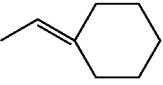 | — | M1: 311(M+1)[Ref13→Meth2] |
| 98 | 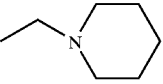 | 2HCl | M1: 314(M+1)[Ex99] |
| 99 | 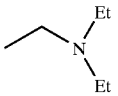 | 2HCl | M1: 302(M+1) |
| 100 | 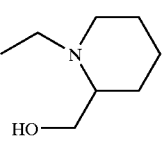 | 2HCl | M1: 344(M+1)[Ref13→Meth2] |
Example VI
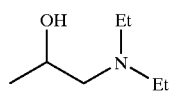
| Ex | Rᶠ | n | salt | DATA |
|---|---|---|---|---|
| 101 | 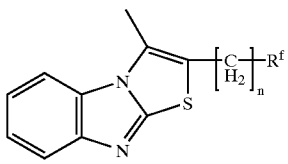 | 0 | 2HCl | M1: 304(M+1)[Ex99→Meth7] |
| 102 | O-iPr | 1 | HCl | M2: 260(M+)[Ref12→Meth9] |

TABLE 1-continued

| # | Structure | | Salt | Data |
|---|---|---|---|---|
| 103 | O-cHex | 1 | HCl | M2: 300(M+)[Ref12→Meth9] |
| 104 | O—CH2-cHex | 1 | HCl | M1: 315(M+1)[Ref12→Meth9] |
| 105 | O—Ph | 1 | HCl | M1: 295(M+1)[Ref12→Meth9] |
| 106 | O-(2-OMe)Ph | 1 | HCl | M1: 325(M+1)[Ref12→Meth9] |
| 107 | O—(CH2)2-Piperidine | 1 | 2HCl | M1: 330(M+1)[Ref12→Meth9] |
| 108 | NH(Et) | 1 | 2HCl | M2: 245(M+)[Ref12→Meth10] |
| 109 | *2-amino-1-propanol-N-methyl* | 1 | 2HCl | M1: 276(M+1)[Ref12→Meth10] |
| 110 | *(1-methylpiperidin-2-yl)methanol* | 1 | 2HCl | M1: 316(M+1)[Ref12→Meth10] |
| 111 | *trans-2-(methylamino)cyclohexanol* | 1 | 2HCl | M1: 316(M+1)[Ref12→Meth10] |
| 112 | *trans-2-(dimethylamino)cyclohexanol* | 1 | 2HCl | M1: 330(M+)[Ex111→Ex88] |
| 113 | *N-ethyl-N-methylacetamide* | 1 | HCl | M2: 287(M+)[Ref12→Meth10] |
| 114 | *N-methylcyclohexanecarboxamide* | 1 | HCl | M1: 328(M+1)[Ex118→Meth8→Meth3] |
| 115 | *2-ethyl-N-methylbutanamide* | 0 | HCl | M1: 302(M+1)[Ex117→Meth8→Meth3] |
| 116 | *N-methylcyclohexanecarboxamide* | 0 | HCl | M1: 314(M+1)[Ex117→Meth8→Meth3] |
| 117 | NH(C=O)O-tBu | 0 | — | NMR(CDCl3)δ 1.49(s,9H)2.64(s,3H)[Ref9→Meth6] |
| 118 | *N-methylphthalimide* | 1 | — | M1: 348(M+1)[Ref12→Meth10] |

TABLE 1-continued

| 119 | [structure: carbamate with N-Et, O-linked to 2-oxocyclohexyl] | 1 | HCl | M1: 386(M+1) |

Regarding typical methods for the synthesis of the example compounds shown in the above table and several of the compounds, other physical property values than those described in the table are shown (NMR: nuclear magnetic resonance spectrum; measured with DMSO-$d_6$, TMS internal standard unless otherwise noted).

In this connection, silica gel was used as the filler of the column chromatography.

EXAMPLE 3

N-Cyclohexyl-N-methylthiazolo[3,2-a]
benzoimidazole-2-carboxamide $SOCl_2$ (20 ml) and then several drops of DMF were added to the compound of Reference Example 8 (2.8 g), and the mixture was heated under reflux for 1 hour. After cooling, the reaction solution was mixed with Tol and stirred, and then the resulting precipitate was collected by filtration to obtain thiazolo[3,2-a]benzoimidazole-2-carboxylic acid chloride. This was suspended in DCE (25 ml), mixed with N-methylcyclohexylamine (2.73 ml) and stirred at room temperature for 1 hour. After completion of the reaction, this was mixed with water, extracted with $CHCl_3$ and dried with anhydrous $MgSO_4$, and then the solvent was evaporated under a reduced pressure. The residue was purified by a column chromatography (eluent; Hex:EtOAc=1:1), and the thus obtained crystals were recrystallized from $CHCl_3$/Hex to obtain the title compound (2.36 g).

EXAMPLE 41

N-Cyclohexyl-6-glycylamino-N-methylthiazolo[3,2-a]benzoimidazole-2-carboxamide dihydrochloride Under ice-cooling, WSC HCl (0.58 g) was added to DMF (15 ml) solution of desalted form of the compound of Reference Example 10 (0.33 g) and N-(t-butoxycarbonyl) glycine (0.53 g), and the mixture was stirred at room temperature for 6 hours. The reaction solution was poured into ice water, and the resulting precipitate was collected by filtration, washed with water and then dried under a reduced pressure. The thus obtained crystals were dissolved in a mixed solvent of MeOH/EtOAc, and this was mixed with 4 M HCl EtOAc solution and further stirred. The resulting precipitate was collected by filtration, washed with EtOAc and then recrystallized from a MeOH/EtOAc mixed solvent to obtain title compound (180 mg).

NMR (DMSO-$d_6$): δ11.29 (s, 1H), 9.20 (brs, 1 H), 8.70 (s, 1 H), 7.85 (br), 7.77 (d, 1 H), 7.57 (d, 1 H), 4.23 (br, 1 H), 3.88 (brd, 2 H), 3.18 (brs, 3 H), 1.00–1.85 (m, 10 H).

EXAMPLE 50

N-Cyclohexyl-N-methyl-6-nitrothiazolo[3,2-a]
benzoimidazole-2-carboxamide

The compound of Example 3 (12.3 g) was dissolved in concentrated sulfuric acid, and this was mixed with fuming nitric acid (1.95 ml) under ice-cooling and then stirred at room temperature for 30 minutes. The reaction solution was poured into ice water and neutralized by adding saturated $NH_3$ aqueous solution, and then the thus formed precipitate was collected by filtration. The thus collected crude crystals were washed with hot MeOH to obtain the title compound (12.7 g).

EXAMPLE 63

N-Cyclohexyl-6-hydroxymethyl-N-methylthiazolo
[3,2-a]benzoimidazole-2-carboxamide hydrochloride The compound of Reference Example 6 (5 g) was mixed with 1 M HCl aqueous solution (50 ml) and stirred, and then water was evaporated under a reduced pressure. The residue was suspended in DMF (50 ml) and mixed with 1-hydroxybenzotriazole (3.6 g) and 1-ethyl-3-(3'-dimethylaminopropyl)carbodiimide hydrochloride (WSC HCl) (11.6 g) at room temperature, and then the mixture was stirred at the same temperature for 2 hours. Next, this was mixed with N-methylcyclohexylamine (5.3 ml) and stirred for 15 minutes and further mixed with water (200 ml) and 1 M NaOH aqueous solution (100 ml) and stirred, and then the resulting precipitate was collected by filtration to obtain desalted form of the title compound (6.1 g). This was made into hydrochloride in the usual way to obtain the title compound.

NMR (DMSO-$d_6$): δ9.15 (br, 1 H), 8.21 (s, 1 H), 7.72 (d, 1 H), 7.42 (d, 1 H), 6.06 (br), 4.69 (s, 2 H), 4.25 (br, 1 H), 3.18 (brs, 3 H), 1.00–1.85 (m, 10 H).

EXAMPLE 64

N-Hydroxymethyl-N-methyl-N-neopentylthiazolo[3,2-a]benzoimidazole-2-carboxamide hydrochloride This was produced from the compound of Reference Example 6 and N-methylneopentylamine in the same manner as described in Example 63.

NMR (DMSO-$d_6$): δ9.27 (s, 1 H), 8.22 (s, 1 H), 7.72–8.21 (br), 7.72–7.74 (m, 1 H), 7.40–7.43 (m, 1 H), 4.70 (brs, 2 H), 3.35–3.55 (m, 5 H), 0.97 (s, 9 H).

EXAMPLE 65

N-Cyclohexyl-7-hydroxymethyl-N-methylthiazolo
[3,2-a]benzoimidazole-2-carboxamide hydrochloride The compound of Reference Example 3 (24 g) was dissolved in THF (100 ml), and this was mixed with THF (60 ml) solution of 1 M tetrabutylammonium fluoride and stirred at room temperature for 1 hour. After evaporation of the solvent under a reduced pressure, the residue was separated and purified by a column chromatography (eluent; Tol:acetone=1:1) and then subjected to usual salt formation reaction to obtain the compound of Example 63 and the title compound, respectively.

NMR (DMSO-d$_6$): δ9.04 (br, 1 H), 8.10 (d, 1 H), 7.70 (s, 1 H), 7.35 (d, 1 H), 6.12 (br), 4.66 (s, 2 H), 4.25 (br, 1 H), 3.18 (br, 3 H), 1.05–1.85 (m, 10 H).

EXAMPLE 66

N-Cyclohexyl-6-formyl-N-methylthiazolo[3,2-a] benzoimidazole

TEA (17 ml) and SO$_3$ Py (16 g) were added to DMSO (60 ml) suspension of desalted form of the compound of Example 63 (12 g), and the mixture was stirred at room temperature for 1 hour. By adding water (300 ml) to the reaction solution while stirring and collecting the resulting precipitate by filtration, the title compound (9.4 g) was obtained.

NMR (DMSO-d$_6$): δ10.09 (s, 1 H), 9.12 (br, 1 H), 8.72 (s, 1 H), 7.95 (dd, 1 H), 7.85 (d, 1 H), 4.26 (br, 1 H), 3.18 (br, 3 H), 1.07–1.85 (m, 10 H).

EXAMPLE 67

6-Formyl-N-methyl-N-neopentylthiazolo[3,2-a] benzoimidazole-2-carboxamide

This was produced from desalted form of the compound of Example 64 in the same manner as described in Example 66.

NMR (DMSO-d$_6$): δ10.10 (s, 1 H), 9.23 (brs, 1 H), 8.71 (s, 1 H), 7.96 (dd, 1 H), 7.86 (d, 1 H), 3.2–3.6 (m, 5 H), 0.97 (s, 9 H).

EXAMPLE 68

N-Cyclohexyl-8-hydroxymethyl-N-methylthiazolo [3,2-a]benzoimidazole-2-carboxamide MeOH (5 ml) solution of the compound of Example 69 (42 mg) was mixed with 1 M NaOH aqueous solution, and the mixture was stirred at room temperature for 1 hour. After evaporation of MeOH under a reduced pressure, the residue was separated between water and EtOAc, and the organic layer was washed with water and saturated brine. After drying with Na$_2$SO$_4$, the solvent was evaporated under a reduced pressure and the resulting residue was washed with a small amount of EtOAc to obtain the title compound (23 mg).

EXAMPLE 69

[2-[Cyclohexyl(methyl)carbamoyl]thiazolo[3,2-a] benzoimidazol-8-yl]methyl acetate hydrochloride A CCl$_4$ (10 ml) solution of the compound of Example 56 (164 mg) was mixed with AIBN (8 mg) and NBS (89 mg) and heated under reflux for 2 hours. After evaporation of the solvent under a reduced pressure, the residue was dissolved in acetic acid (5 ml) and the solution was mixed with sodium acetate (820 mg) and further heated under reflux for 2 hours. After evaporation of the solvent under a reduced pressure, the residue was purified by a column chromatography (eluent; Hex:EtOAc=1:1), made into hydrochloride in the usual way and then washed with EtOAc to obtain the title compound (51 mg).

EXAMPLE 71

6-Formylmethyl-N-methyl-N-neopentylazolo[3,2-a] benzoimidazole-2-carboxamide

In an atmosphere of argon, 60% NaH (0.32 g) was suspended in DMSO (20 ml), (methoxymethyl) triphenylphosphonium chloride (2.87 g) was gradually added thereto and then the mixture was stirred at room temperature for 30 minutes. DMSO (2 ml) solution of the aldehyde compound of Example 67 (0.69 g) was added dropwise to this reaction solution, and the mixture was stirred at room temperature for 8 hours. The reaction solution was poured into ice water and extracted with EtOAc, and the organic layers were combined, washed with water and saturated brine and then dried with anhydrous MgSO$_4$. After removal of the drying agent by filtration, concentration was carried out under a reduced pressure, and the resulting residue was purified by a column chromatography (eluent; Tol:EtOAc=3:1) to obtain a methoxyvinyl compound (0.49 g). THF (5 ml) solution of the thus obtained vinyl compound was mixed with 4 M HCl-EtOAc solution (5 ml) and stirred at room temperature for 2 hours. The reaction solution was neutralized with saturated sodium bicarbonate aqueous solution and extracted with EtOAc, and the combined organic layer was washed with water and saturated brine and then dried with anhydrous MgSO$_4$. After removal of the drying agent by filtration, concentration was carried out under a reduced pressure, and the resulting residue was purified by a column chromatography (eluent; Tol:EtOAc=3:1) to obtain the title compound (0.32 g).

NMR (CDCl$_3$): 9.82 (1 H, t), 8.09 (1 H, s), 7.74–7.79 (1 H, m), 7.53–7.55 (1 H, m), 7.21–7.26 (1 H, m), 3.86–3.89 (2 H, m), 3.32–3.54 (5 H, m), 1.02 (9 H, s).

EXAMPLE 72

N-Methyl-6-[2-[N-(2-methoxyethyl)amino]ethyl]-N-neopentylthiazolo[3,2-a]benzoimidazole-2-carboxamide dihydrochloride 2-Methoxyethylamine (0.18 g), acetic acid (1 ml) and NaB(OAc)$_3$H (0.50 g) were added to a DCE solution of the compound of Example 71 (0.16 g), and the mixture was stirred at room temperature for 8 hours. The reaction solution was neutralized with saturated NaHCO$_3$ aqueous solution and extracted with EtOAc, and the combined organic layer was washed with water and saturated brine and then dried with anhydrous MgSO$_4$. After removal of the drying agent by filtration, concentration was carried out under a reduced pressure, and the resulting residue was purified by a column chromatography (eluent; CHCl$_3$:MeOH=10:1). The thus obtained compound of interest was dissolved in MeOH and treated with 4 M HCl-EtOAc solution to obtain the title compound (0.03 g).

EXAMPLE 73

N-Cyclohexyl-7-[(hydroxy)(1H-imidazol-2-yl) methyl]-N-methylthiazolo[3,2-a]benzoimidazole-2-carboxamide dihydrochloride In an atmosphere of argon, 1.5 M nBuLi-Hex solution (0.5 ml) was added at −78° C. to THF (5 ml) solution of 1-[(2-trimethylsilylethoxy)methyl]imidazole (151 mg), and the mixture was stirred at the same temperature for 30 minutes. This was then added to THF (10 ml) solution of the compound of Example 70 (0.26 g), which had been cooled to −78° C., and the mixture was stirred for 15 minutes. The reaction solution was mixed with water, extracted with EtOAc and washed with saturated brine. After evaporation of the solvent under a reduced pressure, the resulting residue was purified by a column chromatography (eluent; Tol:acetone=2:1~CHCl$_3$:MeOH=10:1) to obtain an alcohol compound (192 mg). An iPrOH (5 ml) solution of this compound was mixed with 3 M hydrochloric acid (20 ml) and heated under reflux for 1 hour. After cooling, the reaction solution was neutralized with NaHCO$_3$ and extracted with CHCl$_3$. After drying with Na$_2$SO$_4$, the solvent was evaporated and the residue was purified by a column chromatography (eluent; CHCl$_3$:MeOH:28% aqueous ammonia=10:1:0.1). The thus obtained compound was converted into hydrochloride in the usual way and then washed with EtOAc-acetone, thereby obtaining the title compound (50 mg).

EXAMPLE 74

[[2-[-Cyclohexyl(methyl)carbamoyl]thiazolo[3,2-a] benzoimidazol-6-yl]methyl] azide NaN$_3$ (0.20 g) and K$_2$CO$_3$ (0.78 g) were added to DMF (5 ml) solution of 6-chloromethyl-N-cyclohexyl-N-methylthiazolo[3,2-a]benzoimidazole-2-carboxamide hydrochloride (0.15 g) produced from the compound of Example 63 in the same manner as described in Example 75, and the mixture was stirred at 80° C. for 15 hours, mixed with a catalytically effective amount of Bu$_4$NI and stirred at 80° C. for 8 hours and then at 120° C. for 15 hours. After cooling, the reaction solution was poured into water and extracted with EtOAc. After drying with MgSO$_4$, the solvent was evaporated to obtain the title compound (0.14 g).

EXAMPLE 75

6-[[(2-Methoxyethyl)amino]methyl]-N-methyl-N-neopentylthiazolo[3,2-a]benzoimidazole-2-carboxamide dihydrochloride Under ice-cooling, the compound of Example 64 (0.99 g) was added to SOCl$_2$ (5 ml) and stirred at the same temperature for 2 hours, and then SOCl$_2$ was evaporated under a reduced pressure to obtain 6-chloromethyl-N-methyl-N-neopentylthiazolo[3,2-a]benzoimidazole-2-carboxamide hydrochloride (1.15 g). The thus obtained compound (200 mg) was dissolved in DMF (10 ml), and the solution was mixed with 2-methoxyethylamine (390 mg) and K$_2$CO$_3$ (1.0 g) and stirred at room temperature for 3 days. The reaction solution was poured into water, extracted with EtOAc, washed with water and saturated brine and dried with MgSO$_4$, and then the solvent was evaporated under a reduced pressure. The resulting residue was purified by a column chromatography (eluent; CHCl$_3$:MeOH:saturated NH$_3$ aqueous solution=10:1:0.1) and then converted into hydrochloride in the usual way to obtain the title compound (160 mg).

NMR: δ9.26–9.48 (br), 9.12 (s, 1 H), 8.21 (s, 1 H), 7.78 (d, 1 H), 7.63 (dd, 1 H), 5.00–5.70 (br), 4.22–4.36 (m, 2 H), 3.60–3.66 (m, 2 H), 3.38–3.53 (m, 5 H), 3.30 (s, 3 H), 3.02–3.18 (m, 2 H), 0.97 (s, 9 H).

EXAMPLE 80

N-Cyclohexyl-6-[[(2-methoxyethyl)amino]methyl]-N-methylthiazolo[3,2-a]benzoimidazole-2-carboxamide dihydrochloride NMR: δ9.53 (brs, 2 H), 8.82–9.26 (br, 1 H), 8.27 (s, 1 H), 7.79 (d, 1 H), 7.68 (dd, 1 H), 4.29 (brt, 2 H), 4.15–4.36 (br, 1 H), 3.66 (t, 2 H), 3.30 (s, 3 H), 3.00–3.30 (m, 5 H), 1.52–1.90 (m, 7 H), 1.28–1.43 (m, 2 H), 1.07–1.25 (m, 1 H).

EXAMPLE 81

6-[(3-Methoxypropylamino)methyl]-N-methyl-N-neopentylthiazolo[3,2-a]benzoimidazole-2-carboxamide dihydrochloride NMR: δ9.30–9.50 (br), 9.14 (s, 1 H), 8.23 (s, 1 H), 7.79 (d, 1 H), 7.66 (dd, 1 H), 5.50–6.20 (br), 4.27 (brt, 2 H), 3.36–3.54 (m, 7 H), 3.22 (s, 3 H), 2.88–3.02 (m, 2 H), 1.86–1.98 (m, 2 H), 0.97 (s, 9 H).

EXAMPLE 83

N-Cyclohexyl-N-methyl-6-morpholinomethylthiazolo[3,2-a]benzoimidazole-2-carboxamide dihydrochloride NMR: δ11.36–11.54 (br, 1 H), 8.75–9.10 (br, 1 H), 8.27 (s, 1 H), 7.79 (d, 1 H), 7.72 (brd, 1 H), 4.48 (brd, 2 H), 4.07–4.37 (br, 3 H), 3.76–3.98 (m, 4 H), 3.02–3.34 (m, 5 H), 1.50–1.85 (m, 7 H), 1.25–1.44 (m, 2 H), 1.07–1.21 (m, 1 H).

EXAMPLE 87

Methyl N-[[2-[cyclohexyl(methyl)carbamoyl] thiazolo[3,2-a]benzoimidazol-6-yl]methyl]-N-methylglycinate dihydrochloride NMR: δ10.65–11.08 (br, 1 H), 8.80–9.20 (br, 1 H), 8.26 (s, 1 H), 7.80 (d, 1 H), 7.61 (dd, 1 H), 4.05–4.80 (br), 3.76 (s, 3 H), 3.05–3.30 (br, 3 H), 2.83 (s, 3 H), 1.50–1.87 (m, 7 H), 1.28–1.43 (m, 2 H), 1.07–1.25 (m, 1 H).

EXAMPLE 88

6-[[N-(2-Methoxyethyl)-N-methylamino]methyl]-N-methyl-N-neopentylthiazolo[3,2-a]benzoimidazole-2-carboxamide 1.5-fumarate Formic acid (12 ml) and 37% formaldehyde aqueous solution (12 ml) were added to desalted form of the compound of Example 75 (2.84 g), and the mixture was stirred at 100° C. for 1 hour. The solvent was evaporated under a reduced pressure and the resulting residue was separated between 1 M HCl aqueous solution and CHCl$_3$. The water layer was neutralized with NaOH, extracted with CHCl$_3$ and dried with anhydrous Na$_2$SO$_4$, and then the solvent was evaporated under a reduced pressure. The resulting residue was purified by a column chromatography (eluent; CHCl$_3$:MeOH:28% NH$_3$ aqueous solution=20:1:0.1), and then the thus obtained oily material was converted into fumarate in the usual way and recrystallized from EtOH to obtain the title compound (2.72 g).

NMR: δ9.07 (s, 1 H), 8.06 (s, 1 H), 7.63 (d, 1 H), 7.32 (dd, 1 H), 6.62 (s, 3 H), 3.73 (s, 2 H), 3.35–3.55 (m, 7 H), 3.24 (s, 3 H), 2.65 (t, 2 H), 2.25 (s, 3 H), 0.96 (s, 9 H).

EXAMPLE 89

N-Cyclohexyl-6-[[N-(2-methoxyethyl)-N-methylamino]methyl]-N-methylthiazolo[3,2-a]benzoimidazole-2-carboxamide 1.5-fumarate NMR: δ8.95 (brs, 1 H), 8.07 (s, 1 H), 7.63 (d, 1 H), 7.34 (dd, 1 H), 6.62 (s, 3 H), 4.15–4.35 (br, 1 H), 3.77 (s, 2 H), 3.52 (t, 2 H), 3.25 (s, 3 H), 3.17 (brs, 3 H), 2.68 (t, 2 H), 2.27 (s, 3 H), 1.74–1.86 (m, 2 H), 1.52–1.74 (m, 5 H), 1.28–1.43 (m, 2 H), 1.07–1.21 (m, 1 H).

EXAMPLE 90

N-[[2-[Cyclohexyl(methyl)carbamoyl]thiazolo[3,2-a]benzoimidazol-6-yl]methyl]-N-methylglycine dihydrochloride The compound of Example 87 (0.11 g) was dissolved in MeOH (5 ml), mixed with 1 M NaOH aqueous solution (0.52 ml) and stirred at room temperature for 6 hours. The reaction solution was neutralized with 1 M HCl, the solvent was evaporated under a reduced pressure and then the residue was purified by a column chromatography. The resulting residue was dissolved in MeOH, mixed with 4 M HCl EtOAc solution and stirred, and then the solvent was evaporated under a reduced pressure to obtain crude crystals. The crude crystals were washed with EtOAc and dried to obtain the title compound (92 mg).

NMR: δ10.20–11.00 (br, 1 H), 8.80–9.20 (br, 1 H), 8.28 (s, 1 H), 7.79 (d, 1 H), 7.61 (dd, 1 H), 4.35–4.75 (br, 2 H), 4.15–4.35 (br, 1 H), 4.13 (brs, 2 H), 3.18 (brs, 3 H), 2.81 (s, 3 H), 1.50–1.87 (m, 7 H), 1.28–1.44 (m, 2 H), 1.05–1.25 (m, 1 H).

EXAMPLE 91

Cyclohexyl 3-methylthiazolo[3,2-a]benzoimidazol-2-yl ketone hydrochloride

The compound of Reference Example 13 (376 mg) was dissolved in THF (30 ml) and then, in an atmosphere of argon and at −78° C., this was mixed with 1.6 M n-BuLi Hex solution (1.5 ml) and stirred at the same temperature for 30 minutes. Next, this was mixed with cyclohexanecarbonyl chloride (40 ml) and further stirred for 30 minutes. After completion of the reaction, this was mixed with water to increase temperature, extracted with EtOAc, washed with 1 M NaOH aqueous solution, water and saturated brine and then dried with anhydrous $Na_2SO_4$. After evaporation of the solvent under a reduced pressure, the residue was purified by a column chromatography (eluent; Hex:EtOAc=4:1). This was converted into hydrochloride and washed with hot acetone to obtain the title compound (320 mg).

EXAMPLE 99

2-Diethylaminoacetyl-3-methylthiazolo[3,2-a]benzoimidazole dihydrochloride

Bromine (1 ml) and concentrated hydrochloric acid (2 ml) were added to an acetic acid (200 ml) solution of 1-(3-methylthiazolo[3,2-a]benzoimidazol-2-yl)ethanone (*Can. J. Chem.*, 45 (23), 2903–2912 (1967)) (2.3 g), and the mixture was stirred at 90° C. for 30 minutes. The reaction solution was cooled to room temperature, and the thus formed precipitate was collected by filtration and washed with EtOAc. Under ice-cooling, a 1.2 g portion of this was added to an acetonitrile (30 ml) solution of diethylamine (3 ml), and the mixture was stirred at the same temperature for 30 minutes. The reaction solution was mixed with water, extracted with EtOAc, washed with water and saturated brine and dried with anhydrous $Na_2SO_4$, and the solvent was evaporated under a reduced pressure. The resulting residue was purified by a column chromatography (eluent; Hex:EtOAc=2:1~1:1) and further converted into hydrochloride in the usual way to obtain the title compound (355 mg).

EXAMPLE 119

2-Oxocyclohexyl 7-ethyl-N-[(3-methylthiazolo[3,2-a]benzoimidazol-2-yl)methyl]carbamate hydrochloride A DMF (15 ml) solution of desalted form of the compound of Example 108 (840 mg) was mixed with $K_2CO_3$ (1.42 g) and 2-chlorocyclohexanone (0.783 ml) and stirred at 100° C. for 4 hours. After cooling to room temperature, the reaction solution was mixed with water, extracted with EtOAc, washed with water and saturated brine and then dried with $Na_2SO_4$. After evaporation of the solvent under a reduced pressure, the resulting residue was purified by a column chromatography (eluent; EtOAc:$CHCl_3$=1:2), converted into hydrochloride in the usual way and then washed with hot acetone to obtain the title compound (223 mg) as colorless crystals.

The following compounds can also be synthesized using similar production methods of these examples or general synthesis methods.

TABLE 2

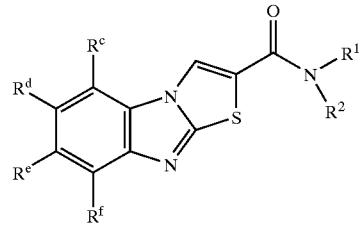

| Ex | $R^1$ | $R^2$ | $R^c$ | $R^d$ | |
|---|---|---|---|---|---|
| 120 | cHex | Me | ⟋⟍N(H)⟋⟍OH | H | |
| 121 | cHex | Me | H | H | |
| 122 | cHex | Me | H | H | |
| 123 | cHex | H | H | ⟋⟍N(H)⟋⟍OH | |
| 124 | cHex | H | H | H | |

TABLE 2-continued
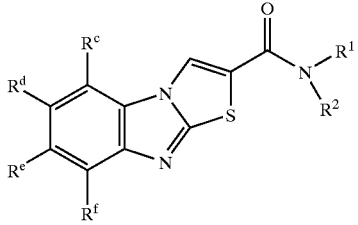
| No. | Rc | Rd | R1/R2 | Rf |
|---|---|---|---|---|
| 125 | cHex | Me | 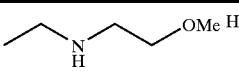 | H |
| 126 | cHex | Me H | | H |
| 127 | cHex | Me H | | H |
| 128 | cHex | H H | 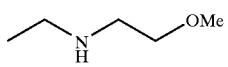 | |
| 129 | cHex | H H | | H |
| 130 | cHex | Me | 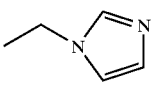 | H |
| 131 | cHex | Me H | | H |
| 132 | cHex | H H | 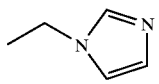 | |
| 133 | cHex | H H | | H |
| 134 | cHex | Me | 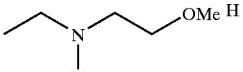 | H |
| 135 | cHex | Me H | | H |
| 136 | cHex | Me H | | H |
| 137 | cHex | H H | 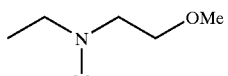 | |
| 138 | cHex | Me H | | H |
| 139 | neo-Pen | Me | 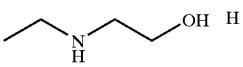 | H |
| 140 | neo-Pen | Me H | | H |
| 141 | neo-Pen | Me H | | H |
| 142 | neo-Pen | H H | 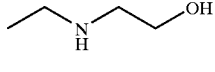 | |
| 143 | neo-Pen | H H | | H |
| 144 | neo-Pen | Me | 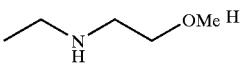 | H |
| 145 | neo-Pen | Me H | | H |
| 146 | neo-Pen | Me H | | H |
| 147 | neo-Pen | H H | 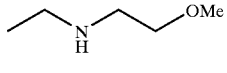 | |
| 148 | neo-Pen | H H | | H |

TABLE 2-continued

| # | R | Rᶜ | Rᵈ | R¹ | R² |
|---|---|---|---|---|---|
| 149 | neo-Pen | Me | | -CH₂CH₂-(1-ethyl-imidazol-2-yl) group | H |
| 150 | neo-Pen | Me | H | | H |
| 151 | neo-Pen | H | H | | -CH₂CH₂-(1-ethyl-imidazol-2-yl) group |
| 152 | neo-Pen | H | H | | H |
| 153 | neo-Pen | Me | | -CH₂CH₂-N(Me)-CH₂CH₂-OMe | H |
| 154 | neo-Pen | Me | H | | H |
| 155 | neo-Pen | Me | H | | H |
| 156 | neo-Pen | H | H | | -CH₂CH₂-N(Me)-CH₂CH₂-OMe |
| 157 | neo-Pen | H | H | | H |
| 158 | neo-Pen | Me | | -CH₂CH₂-morpholinyl | H |
| 159 | neo-Pen | Me | H | | H |
| 160 | neo-Pen | H | H | | -CH₂CH₂-morpholinyl |
| 161 | neo-Pen | H | H | | H |
| 162 | cHept | Me | H | | -CH₂CH₂-morpholinyl |
| 163 | CH₂-cPen | Me | H | | -CH₂CH₂-morpholinyl |
| 164 | norbornyl | Me | H | | -CH₂CH₂-morpholinyl |
| 165 | 2-Me-cyclohexyl | Me | H | | -CH₂CH₂-morpholinyl |

TABLE 2-continued

[Structure: benzimidazo-thiazole carboxamide core with substituents Rc, Rd, Re, Rf on benzene ring and R1, R2 on amide nitrogen]

| Ex | Rd | Rc | (amide substituent) |
|---|---|---|---|
| 166 | 1-ethyl-1-methylcyclopropyl | Me | H / N-ethylmorpholine |
| 269 | cHex | Me | H / 2-methoxyethylmorpholine |
| 270 | cHex | Me | H / 2-ethoxyethylmorpholine |

| Ex | Re | Rf |
|---|---|---|
| 120 | H | H |
| 121 | –CH2CH2–NH–CH2CH2–OH | H |
| 122 | H | –CH2CH2–NH–CH2CH2–OH |
| 123 | H | H |
| 124 | –CH2CH2–NH–CH2CH2–OH | H |
| 125 | H | H |
| 126 | H | –CH2CH2–NH–CH2CH2–OMe |
| 127 | –CH2CH2–NH–CH2CH2–OMe | H |
| 128 | H | H |
| 129 | –CH2CH2–NH–CH2CH2–OMe | H |
| 130 | H | H |
| 131 | H | –CH2CH2–(1-imidazolyl) |
| 132 | H | H |
| 133 | –CH2CH2–(1-imidazolyl) | H |
| 134 | H | H |

TABLE 2-continued

| No. | R1 | R2 |
|---|---|---|
| 135 | -N(Me)CH₂CH₂OMe | H |
| 136 | H | -N(Me)CH₂CH₂OMe |
| 137 | H | H |
| 138 | -N(Me)CH₂CH₂OMe | H |
| 139 | H | H |
| 140 | -NHCH₂CH₂OH | H |
| 141 | H | -NHCH₂CH₂OH |
| 142 | H | H |
| 143 | -NHCH₂CH₂OH | H |
| 144 | H | H |
| 145 | -NHCH₂CH₂OMe | H |
| 146 | H | -NHCH₂CH₂OMe |
| 147 | H | H |
| 148 | -NHCH₂CH₂OMe | H |
| 149 | H | H |
| 150 | H | -CH₂-(1-imidazolyl) |
| 151 | H | H |
| 152 | -CH₂-(1-imidazolyl) | H |
| 153 | H | H |

TABLE 2-continued

| No. | R¹ | R² |
|---|---|---|
| 154 | CH₂CH₂N(Me)CH₂CH₂OMe | H |
| 155 | H | CH₂CH₂N(Me)CH₂CH₂OMe |
| 156 | H | H |
| 157 | CH₂CH₂N(Me)CH₂CH₂OMe | H |
| 158 | H | H |
| 159 | H | CH₂CH₂-morpholinyl |
| 160 | H | H |
| 161 | CH₂CH₂-morpholinyl | H |
| 162 | H | H |
| 163 | H | H |
| 164 | H | H |
| 165 | H | H |
| 166 | H | H |
| 269 | H | H |
| 270 | H | H |

(Test Methods)

Effects of the compounds of the invention were confirmed by the following test methods.

1. mGluR1 Binding Action

An evaluation system which uses mGluR1 expression cells is known as a method for confirming effects of compounds that act upon mGluR1, but this evaluation system is complex due, e.g., to the use of cells.

Thus, a more convenient test method described in the following, namely a binding test which uses tritium-labeled 6-amino-N-cyclohexyl-N,3-dimethylthiazolo[3,2-a]benzoimidazole-2-carboxamide (WO 99/44639) that shows selective and strong action upon mGluR1, was used.

This compound has a high inhibition activity of IC$_{50}$=24 nM for the reaction of glutamic acid in a phosphatidylinositol (PI) hydrolysis system which uses an mGluR1 α expression cell (*Nature*, 383, 89–92, 1996).

(Method for Producing [³H]-(6-amino-N-cyclohexyl-N,3-dimethylthiazolo[3,2-a]benzoimidazole-2-carboxamide))

The tritium-labeled compound used in the binding test was produced by carrying out selective N-methylation of the amide of 6-amino-N-cyclohexyl-N,3-dimethylthiazolo[3,2-a]benzoimidazole-2-carboxamide which had been synthesized from 3-methylthiazolo[3,2-a]benzoimidazole-2-carboxylic acid and cyclohexylamine in accordance with Production Example 1 described in WO 99/44639, in DMF using NaH and [³H]-methyl iodide (CT₃I). Specific activity; 83 Ci/mmol (Amersham)

(Preparation of Rat Cerebellum P2 Membrane Fraction)

Rats (Wistar, males, 9 to 12 weeks of age) were decapitated to excise cerebella. After weight measurement, they were homogenized in 7 to 10 volumes of 0.32 M sucrose solution. After 15 minutes of centrifugation at 900×g, the supernatant was preserved in a container (in ice). The precipitate was again homogenized in 0.32 M sucrose solution of the same volume of the first time and centrifuged at 900×g for 15 minutes. The supernatant obtained this time was combined with the previously obtained supernatant and centrifuged at 15,000×g for 20 minutes. The precipitate was homogenized in 5 mM Tris-HCl, pH 7.4, and centrifuged at 15,000×g for 15 minutes. This step was repeated again. The precipitate was homogenized in 50 mM Tris-HCl, pH 7.4, and centrifuged at 15,000×g for 15 minutes. The precipitate was homogenized in an appropriate amount of 50 mM Tris-HCl, pH 7.4, subdivided into small portions and then preserved at −80° C.

(Binding Test)

The binding test was carried out by the following modified method of Thomsen et al.

As the assay buffer, 50 mM Tris-HCl, 2.5 mM $CaCl_2$, pH 7.4, was used. [$^3$H]-6-Amino-N-cyclohexyl-N,3-dimethylthiazolo[3,2-a]benzoimidazole-2-carboxamide (specific activity; 83 Ci/mmol; Amersham), a test compound and about 0.1 mg of the rat cerebellum P2 membrane fraction were suspended in the buffer to a total volume of 200 μl, dispensed into each of test tubes or wells of a 96 well microplate and then incubated at room temperature (about 25° C.) for 45 minutes. Completion of the incubation was effected by a filtration method using Whatman GF/B filter. Quantity of the radioactivity was measured using a liquid scintillation counter. The $K_D$ value in the saturation test was 47 nM, and $B_{max}$ was 3.9 pmol/mg protein. About 20 nM of [$^3$H]-6-amino-N-cyclohexyl-N,3-dimethylthiazolo[3,2-a] benzoimidazole-2-carboxamide was used in the competitive test, and the specific binding was defined as a portion of the total binding, which was replaced by 10 μM of N-cyclohexyl-6-glycylamino-N-methylthiazolo[3,2-a] benzoimidazole-2-carboxamide (Example 41, $IC_{50}$=20 nM, a PI hydrolysis system using mGluR1 α expression cells). Evaluation of the test compound was carried out by calculating the ratio of binding inhibition upon specific binding.

Determination of protein was carried out using BIO-RAD DC protein assay (BIO-RAD). Bovine serum albumin was used as the standard substance.

Reference Document

Thomsen C., Mulvihill E. R., Haldeman B., Pickering D. S., Hampson D. R. and Suzdak P. D., A pharmacological characterization of the mGluR1 alpha subtype of the metabotropic glutamate receptor expressed in a cloned baby hamster kidney cell line., Brain Res., Aug. 13, 1993, 619 (1–2), 22–8.

As a result of the above test, it was confirmed that a compound having stronger activity among the compounds of the invention has strong affinity for mGluR1 with an $IC_{50}$ value of from $10^{-9}$ M.

In this connection, mGluR1 antagonism of the compound of the invention was confirmed in accordance with the methods described in the following references.

Aronica E., Condorelli D. F., Nicoletti F., Dell'Albani P., Amico C. and Balazs R. (1993), Metabotropic glutamate receptors in cultured cerebellar granule cells: developmental profile., J. Neurochem., 60: 559–565

Santi M. R., Ikonomovic S., Wroblewski J. T. and Grayson D. R. (1994), Temporal and depolarization-induced changes in the absolute amounts of mRNAs encoding metabotropic glutamate receptors in cerebellar granule neurons in vitro., J. Neurochem., 63: 1207–1217

Aronica E., Dell'Albani P., Condorelli D. F., Nicoletti F., Hack N. and Balazs R. (1993), Mechanisms underlying developmental changes in the expression of metabotropic glutamate receptors in cultured cerebellar granule cells: homologous desensitization and interactive effects involving N-Methyl-D-aspartate receptors., Mol. Pharmacol., 44: 981–989

2. In vivo Cerebral Infarction Inhibition Action (MCA Permanent Occlusion Model)

The compound of the invention was dissolved in physiological saline and adjusted to 6 mg/3 ml.

In accordance with J. Pharmacol. Exp. Thr., 276, 84–92, 1996, the left-side MCA of a Fischer-344 rat was permanently occluded, and 24 hours of continuous intravenous infusion of the compound of the invention was started 5 minutes thereafter at a dose of 6 mg/3 ml/kg/h without anesthesia and restriction. After completion of the administration, the animal was decapitated to excise the brain which was subsequently stained with 2,3,5-triphenyltetrazolium hydrochloride (TTC) to measure the infarction volume.

Results

As a result of the above test, the compound of the invention having strong affinity for mGluR1 clearly showed the effect to reduce cerebral infarction volume in an animal model of cerebral infarction having an infarction area caused by local ischemia. Based on these results, it was confirmed that the compound of the invention having strong affinity for mGluR1, particularly mGluR1 antagonism, is a drug useful for the treatment of cerebral infarction, particularly acute phase cerebral infarction.

INDUSTRIAL APPLICABILITY

According to the invention, a novel thiazolobenzoimidazole derivative which acts upon mGluR1 is provided.

Accordingly, the compound of the invention is useful as an agent for the prevention and treatment of diseases, preferably cerebral infarction, in which mGluR1 is considered to be taking a role.

It also relates to novel intermediates which are useful for the synthesis of the compound (I) of the invention.

What is claimed is:

1. A thiazolobenzoimidazole derivative represented by the following general formula (I) or a salt thereof

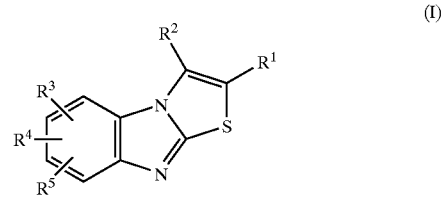

(I)

wherein each of the symbols is defined as follows $R^1$:
 (1) —$A^1$—CO—N($R^6$)—$R^7$, or
 (3) —$A^1$—CO—$A^3$—N($R^6$)—$R^7$,
  $A^1$: a bond,
  $R^6$ and $R^7$: the same or different from each other and each represents hydrogen, —N($R^{15}$)—$R^{16}$, a lower alkyl which may be substituted, a cycloalkyl which may be substituted or a hetero ring which may be substituted and may have bridge(s),
  with the proviso that $R^6$ and $R^7$, together with the adjacent nitrogen atom, may form a hetero ring which may have a substituent and other hetero atom(s), and
  when $R^1$ is —$A^1$—CO—N($R^6$)—$R^7$, $R^2$ is methyl, $A^1$ is a bond, and one of $R^6$ and $R^7$ is a hydrogen, the other is not n-propyl substituted by nicotinamide,
  $R^{15}$ and $R^{16}$: the same or different from each other and each represents hydrogen, —CO-lower alkyl, —CO-halo-lower alkyl or —$COOR^{14}$,
  $A^3$: a lower alkylene group which may be substituted by hydroxyl group(s), $R^2$: hydrogen, a lower alkyl, a halo-lower alkyl, a hydroxy-lower alkyl, a lower alkyl-O-lower alkyl, an amino-lower alkyl or a (mono-or di-lower alkylamino)-lower alkyl group, $R^3$, $R^4$ and $R^5$: the same or different from one another and each represents hydrogen, a halo, a lower alkyl, a halo-lower alkyl, an $N_3$-lower alkyl, a hydroxy-lower alkyl, hydroxy, a lower alkyl-O—, cyano, —COOR$^{14}$, acyl, a formyl-lower alkyl, an acyl-O—, an acyl-O-lower alkyl, nitro, —A$^4$—N(R$^{12}$)—(R$^{13}$), —SO$_3$H or —A$^5$—O—A$^4$—N(R$^{12}$)—(R$^{13}$) group, $R^{12}$ and $R^{13}$: the same or different from each other and each represents hydrogen, a —CO—lower alkyl-N(R$^{15}$)—R$^{16}$, a —CO-halo-lower alkyl group, a lower alkyl which may be substituted or a hetero ring group which may be substituted, with the proviso that $R^{12}$ and $R^{13}$, together with the adjacent nitrogen atom, may form a hetero ring which may have a substituent and other hetero atom(s), and when $R^{12}$ and $R^{13}$ are hydrogen at the same time, A$^4$ is other than a bond, R$^{14}$: hydrogen or a lower alkyl group, A$^4$: a bond or a lower alkylene group which may be substituted by hydroxyl group(s), and A$^5$: a bond or a lower alkylene group.

2. The compound or a salt thereof according to claim 1, wherein $R^1$ is —A$^1$—CO—N(R$^6$)—R$^7$.

3. A compound, or a salt thereof, selected from 6-{[(2-methoxyethyl)amino]methyl}-N-methyl-N-neopentylthiazolo[3,2-a]benzoimidazole-2-carboxamide, N-cyclohexyl-6-{[(2-methoxyethyl)amino]methyl}-N-methylthiazolo[3,2-a]benzoimidazole-2-carboxamide, 6-{[(3-methoxypropyl)amino]methyl}-N-methyl-N-neopentylthiazolo[3,2-a]benzoimidazole-2-carboxamide, N-cyclohexyl-N-methyl-6-morpholinomethylthiazolo[3,2-a]benzoimidazole-2-carboxamide, methyl N-{[2-[cyclohexyl(methyl)carbamoyl]thiazolo[3,2-a]benzoimidazol-6-yl]methyl}-N-methylglycinate, 6-{[N-(2-methoxyethyl)-N-methylamino]methyl}-N-methyl-N-neopentylthiazolo[3,2-a]benzoimidazole-2-carboxamide, N-cyclohexyl-6-{[N-(2-methoxyethyl)-N-methylamino]methyl}-N-methylthiazolo[3,2-a]benzoimidazole-2-carboxamide and N-({2-[cyclohexyl(methyl)carbamoyl]thiazolo[3,2-a]benzoimidazol-6-yl}methyl)-N-methylglycine.

4. A pharmaceutical composition which comprises, as an active ingredient, the compound of claim 1 or a pharmaceutically acceptable salt thereof.

* * * * *